United States Patent [19]

Asada et al.

[11] Patent Number: 4,898,822
[45] Date of Patent: Feb. 6, 1990

[54] PROCESS FOR PREPARING OPTICALLY ACTIVE INDOLINE-2-CARBOXYLIC ACID

[75] Inventors: Masanori Asada, Takasago; Shigeki Hamaguchi; Hidetoshi Katsuki, both of Kobe; Yoshio Nakamura, Takasago; Hideyuki Takahashi, Kakogawa, all of Japan; Kenji Takahara, Bronx, N.Y.; Yoshio Shimada, Kakogawa, Japan; Takehisa Ohashi, Kobe, Japan; Kiyoshi Watanabe, Akashi, Japan

[73] Assignee: Kanegafuchi Kagaku Kogyo Kabushiki Kaisha, Osaka, Japan

[21] Appl. No.: 846,436

[22] Filed: Mar. 31, 1986

[30] Foreign Application Priority Data

Apr. 1, 1985 [JP] Japan .................................. 60-69769
May 20, 1985 [JP] Japan .................................. 60-109160
Jun. 8, 1985 [JP] Japan .................................. 60-124879

[51] Int. Cl.$^4$ .......................... C12P 17/10; C12P 1/04; C12N 9/18; C07P 41/00
[52] U.S. Cl. .................................... 435/121; 435/136; 435/280; 435/197; 435/110; 435/839; 435/897; 435/830; 435/813; 435/874; 435/925; 435/921; 435/911; 435/170
[58] Field of Search ............... 435/180, 280, 220, 223, 435/224, 225, 197, 198, 135, 136, 117, 118, 119, 822, 120, 121

[56] References Cited

U.S. PATENT DOCUMENTS 4,486,241 11/1984 Schouten ............................. 548/491

OTHER PUBLICATIONS

Ghisalba et al., *Nachri Chem. Tech. Lab.* 34, pp. 973–982, 1986.
Patent Abstracts of Japan, vol. 10, No. 269 (C-372)[2325], 12th Sept. 1986; & JP-A-61 92 595, 596.
Patent Abstracts of Japan, vol. 11, No. 141 (C-421)[2588], 8th May 1987; & JP-A-61 282 093.

*Primary Examiner*—Charles F. Warren
*Assistant Examiner*—Irene Marx
*Attorney, Agent, or Firm*—Armstrong, Nikaido, Marmelstein, Kubovcik & Murray

[57] ABSTRACT

A process for preparing optically active indoline-2-carboxylic acid by an optical resolution, which comprises subjecting a racemic ester of (R,S)-indoline-2-carboxylic acid having the general formula [(R,S)-I] to the action of an enzyme or a microorganism having a stereoselective esterase activity, which is capable of asymmetrically hydrolyzing the racemic ester [(R,S)-I] to give optically active indoline-2-carboxylic acid having the formula [II*] so as to produce the hydrolysis product, i.e. optically active indoline-2-carboxylic acid [II*] and an unreacted optically active ester of indoline-2-carboxylic acid having the general formula [I*], isolating each optically active form, and further, if necessary, hydrolyzing the obtained optically active ester [I*] to give an optical antipode of the acid [II*].

According to the process of the present invention, optically active indoline-2-carboxylic acid with a high optical purity can be prepared in a simple process with a good yield.

9 Claims, No Drawings

PROCESS FOR PREPARING OPTICALLY ACTIVE INDOLINE-2-CARBOXYLIC ACID

BACKGROUND OF THE INVENTION

The present invention relates to a process for preparing optically active indoline-2-carboxylic acid by an optical resolution, which comprises subjecting a racemic ester of (R,S)-indoline-2-carboxylic acid having the general formula [(R,S)-I]:

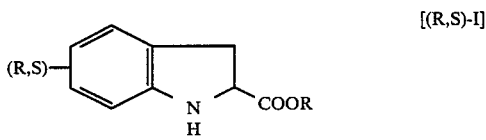

wherein R is an alkyl or alkenyl group having 1 to 10 carbon atoms; an alkyl or alkenyl group having 1 to 10 carbon atoms substituted with either hydroxyl group or a halogen atom, or simultaneously substituted with both hydroxyl group and a halogen atom; a substituted or unsubstituted aromatic hydrocarbon group; or substituted or unsubstituted phenyl or benzyl group, to the action of an enzyme or a microorganism having a stereo-selective esterase activity, which is capable of asymmetrically hydrolyzing the racemic ester [(R,S)-I] to give optically active indoline-2-carboxylic acid having the formula [II*]:

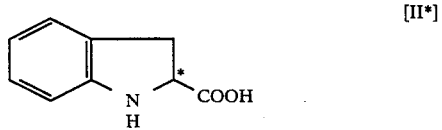

so as to produce the hydrolysis product, i.e. optically active indoline-2-carboxylic acid [II*] and an unreacted optically active ester of indoline-2-carboxylic acid having the general formula [I*]:

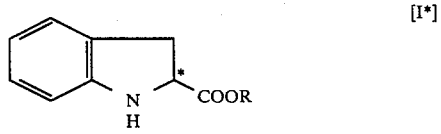

wherein R is as above, isolating each optically active form, and further, if necessary, hydrolyzing the obtained optically active ester [I*] to give an optical antipode of the acid [II*].

The present invention also relates to a process for preparing optically active indoline-2-carboxylic acid by immobilizing the microorganism or the enzyme on the support and utilizing the affinity difference between indoline-2-carboxylic acid and ester of indoline-2-carboxylic acid to the immobilizing support, which comprises eluting hydrophilic optically active indoline-2-carboxylic acid with water or a buffer solution, and then hydrolyzing with alkali optically active ester of indoline-2-carboxylic acid which is adsorbed and retained on the support, followed by elution of optically acitve indoline-2-carboxylic acid [II*] which has an opposite optical rotation based on the previously obtained optically active indoline-2-carboxylic acid.

The process of the present invention can produce (R)-indoline-2-carboxylic acid and ester of (S)-indoline-2-carboxylic acid, (S)-indoline-2-carboxylic acid and ester of (R)-indoline-2-carboxylic acid, or simultaneously both (R)- and (S)-indoline-2-carboxylic acids.

These optically active indoline-2-carboxylic acids can be used as a starting material for synthesizing various kinds of drug. For example, (S)-indoline-2-carboxylic acid can be used for synthesizing (S)-1-[(S)-mercapto-2-oxopropyl]-indoline-2-carboxylic acid having the formula:

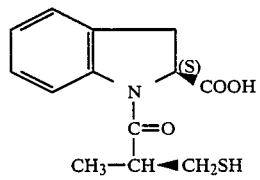

which is an antihypertensive drug effective as an inhibitor for Angiotensin I converting enzyme, and the like (J. Med. Chem. 26, 394 (1983)).

Hitherto, these optically active indoline-2-carboxylic acids have been prepared by using the agent for optical resolution as follows:

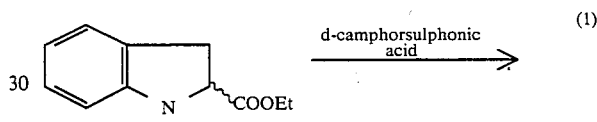

(Japanese unexamined Patent Publication No. 81460/1982)

(M. Vincent el al., Tetrahedron Letters, 23, 1677 (1982))

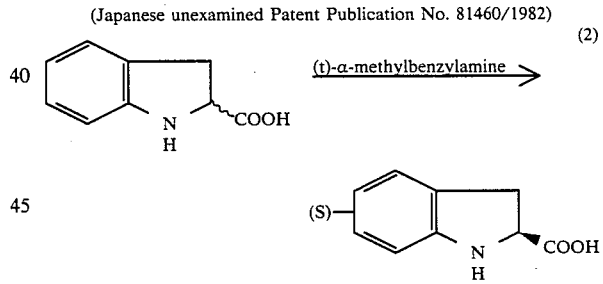

(S)-form is extracted from mother liquid.
(J. Med. Chem., 26, 1267 (1983))

However, these processes are too complicated and thus more simple process for preparing optically active indoline-2-carboxylic acid or optically active ester of indoline-2-carboxylic acid has been desired for the production on a large scale.

The present inventors have studied, in order to establish a simple process for preparing optically active indoline-2-carboxylic acid, by esterifying indoline-2-carboxylic acid with various alcohols and then subjecting the obtained ester to the action of a microorganism or an enzyme. As the result, it was found by the present inventors as follows:

(1) Racemic ester of (R,S)-indoline-2-carboxylic acid was subjected to the action of an enzyme derived from the animal pancreas; the microorganism of the genus such as Aspergillus, Bacillus, Streptomyces, Arthrobacter, Saccharomyces, Aeromonas, Acidiphilium, Brevibacterium, Corynebacterium, Trichosporon or Pseudomonas; or an enzyme derived from any of these microorganisms to be asymmetrically hydrolyzed to give (R)-indoline-2-carboxylic acid and ester of (S)-indoline-2-carboxylic acid, which were then separated and extracted with an organic solvent to give (R)-indoline-2-carboxylic acid [(R)-II] and ester of (S)-indoline-2-carboxylic acid [(S)-I], further [(S)-I] being hydrolyzed with alkali or an enzyme to give (S)-indoline-2-carboxylic acid [(S)-II].

(2) Racemic ester of (R,S)-indoline-2-carboxylic acid was subjected to the action of the microorganism of the genus such as Alcaligenes, Nadsonia, Rhodotorula, Torulopsis, Protaminobacter, Pseudomonas, Arthrinium, Aspergillus, Cephalosporium, Echinopodospora, Emericellopsis, Hypocrea, Isaria, Lepista, Nectria, Phialophora, Pestalotiopsis, Podospora, Moniliella, Kluyveromyces, Schizosaccharomyces, Wickerhamia, Arthrobacter, Brevibacterium, Botryoascus, Candida, Citeromyces, Debaryomyces or Hormoascus, or an enzyme derived from any of these microorganisms to be asymmetrically hydrolyzed to give (S)-indoline-2-carboxylic acid [(S)-II] and ester of (R)-indoline-2-carboxylic acid [(R)-I], which were then separated and extracted with an organic solvent to give [(S)-II] and [(R)-I], further [(R)-I] being hydrolyzed with alkali or an enzyme to give [(R)-II].

(3) The above enzyme or microorganism was immobilized on a hydrophobic support so that, by utilizing an affinity difference between indoline-2-carboxylic acid and ester of indoline-2-carboxylic acid to the immobilizing support, hydrophilic indoline-2-carboxylic acid was eluted with water or a buffer solution and then ester of indoline-2-carboxylic acid, which was adsorbed and retained on the support, was hydrolyzed with alkali to elute optically active indoline-2-carboxylic acid [II*] which had an opposite optical rotation based on the previously obtained optically active indoline-2-carboxylic acid.

Hitherto, it has not yet been reported that optically active indoline-2-carboxylic acid can be prepared by the asymmetric hydrolysis of ester of indoline-2-carboxylic acid with enzyme or microorganism, that racemic ester of indoline-2-carboxylic acid is asymmetrically hydrolyzed with immobilized enzyme while the reaction product is simultaneously separated, and then unreacted ester adsorbed on the support is hydrolyzed with alkali, the product of hydrolysis being eluted, and that these processes can be carried out continuously.

SUMMARY OF THE INVENTION

In accordance with the present invention, there can be provided a process for preparing (R)-indoline-2-carboxylic acid having the formula [(R)-II]:

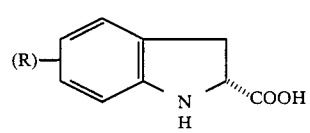

by an optical resolution, a process for preparing (S)-indoline-2-carboxylic acid having the formula [(S)-II]:

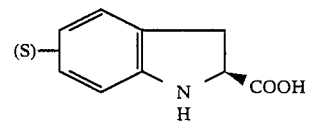

by an optical resolution, and a process for preparing optically active indoline-2-carboxylic acid having the formula [II*]:

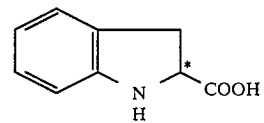

DETAILED DESCRIPTION OF THE INVENTION

Examples of ester of indoline-2-carboxylic acid having the general formula [(R,S)-I]:

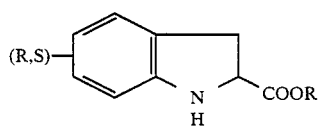

wherein R is an alkyl or alkenyl group having 1 to 10 carbon atoms; and alkyl or alkenyl group having 1 to 10 carbon atoms substituted with either hydroxyl group or a halogen atom, or simultaneously substituted with both hydroxyl group and a halogen atom; a substituted or unsubstituted aromatic hydrocarbon group; or substituted or unsubstituted phenyl or benzyl group, which is used as a substrate in the present invention, are esters with, for instance, methanol, ethanol, propanol, butanol, amino alcohol, hexanol, heptanol, octanol, ethylene glycol, glycerol, glycerol-α-monochlorohydrin, 2,3-dichloro-1-propanol or 1,3,5-pentanetriol.

Ester of indoline-2-carboxylic acid [(R,S)-I] can be obtained as follows: i.e. to (R,S)-indoline-2-carboxylic acid is added alcohol, which serves as both solvent and reaction reagent, to conduct condensation reaction in 5 to 40% (W/V) concentration of indoline-2-carboxylic acid under strong acidic condition at a temperature ranging from 50° C. to reflux temperature for 1 to 5 hours. Then, to the reaction mixture a saturated aqueous solution of sodium bicarbonate is added to adjust to pH 7, followed by extraction with a hydrophobic organic solvent such as ethyl acetate, chloroform, methylene chloride, toluene or hexane, and further concentration to give ester of (R,S)-indoline-2-carboxylic acid [(R,S)-I] with a high purity.

Examples of microorganism which has a stereoselective activity for asymmetrically hydrolyzing racemic ester [(R,S)-I] to give [(R)-II] are those of genus such as, for instance, Arthrobacter, Saccharomyces, Aeromonas, Acidiphilium, Brevibacterium, Corynebacterium, Trichosporon or Pseudomonas, more especially *Pseudomonas aeruginosa, Aspergillus niger, Aspergillus melleus, Bacillus subtilis, Streptomyces griseus, Saccharomyces cerevisiae, Trichosporon cutaneum, Aeromonas hydrophila, Arthrobacter paraffineus, Arthrobacter nicotianae, Acidiphilium cryptum, Brevibacterium protophormiae, Corynebacterium paurometabolum, Corynebacterium acetoacidophilum* or *Pseudomonas oxalacticus,* more especially *Arthrobacter paraffineus* ATCC 21317, *Saccharomyces cerevisiae* HUT 7018, *Aeromonas hydrophila* IFO 3820, *Acidiphilum cryptum* IFO 14242, *Brevibacterium protophormiae* IFO 12128, *Corynebacterium paurometabolum* IFO 12160, *Trichosporon cutaneum* IFO 1200, *Pseudomonas oxalacticus* IFO 13593 and the like.

Examples of microorganism which has a stereoselective esterase activity capable of asymmetrically hydrolyzing racemic ester [(R,S)-I] to give [(S)-II] are those of the genus such as, for instance, Alcaligenes, Nadsonia, Rhodotorula, Torulopsis, Protaminobacter, Pseudomonas, Arthrinium, Aspergillus, Cephalosporium, Echinopodospora, Emericellopsis, Hypocrea, Isaria, Lepista, Nectria, Phialophora, Pestalotiopsis, Podospora, Moniliella, Kluyveromyces, Schizosaccharomyces, Wickerhamia, Arthrobacter, Brevibacterium, Botryoascus, Candida, Citeromyces, Debaryomyces or Hormoascus, more especially *Arthrinium phaeospermum, Aspergillus ficuum, Cephalosporium mycophilum, Echinopodospora jamaicensis, Emericellopsis glabra, Hypocrea lactea, Isaria atypicola, Lepista nuda, Nectria flammea, Pestalotiopsis distincta, Phialophora fastigiasta, Podospora carbonaria, Botryoascus synnaedendrus, Candida diversa, Candida pseudotropicalis, Citeromyces matritensis, Debaryomyces hansenii, Hormoascus platypodis, Moniliella tomentosa, Kluyveromyces fragilis, Nadsonia elongata, Rhodotorula glutinis, Schizosaccharomyces pombe, Torulopsis gropengiesseri, Wickerhamia fluorescens, Alcaligenes faecalis, Arthrobacter crystallopoietes, Brevibacterium flavum, Protaminobacter alboflavus* or *Pseudomonas acidovorans,* more especially *Alcaligenes faecalis* IFO 12669, *Nadsonia elongata* IFO 0665, *Rhodotorula glutinis* IAM 4642, *Torulopsis gropengiesseri* IFO 0659, *Protaminobacter alboflavus* IFO 3707, *Pseudomonas acidovorans* IFO 13582, *Arthrinium phaeospermum* IFO 5703, *Aspergillus ficuum* IFO 4280, *Cephalosporium mycophilum* IFO 8580, *Echinopodospora jamaicensis* IFO 30406, *Emericellopsis glabra* IFO 9031, *Hypocrea lactea* IFO 8434, *Isaria atypicola* IFO 9205, *Lepista nuda* IFO 8104, *Nectria flammea* IFO 30306, *Phialophora fastigiata* IFO 6850, *Pestalotiopsis distincta* IFO 9981, *Podospora carbonaria* IFO 30294, *Moniliella tomentosa* CBS 22032, *Kluyveromyces fragilis* IFO 0288, *Schizosaccharomyces pombe* IFO 0347, *Wickerhamia fluorescens* IFO 1116, *Arthrobacter crystallopoietes* IFO 14235, *Brevibacterium flavum* ATCC 21269, *Botryoascus synnaedendrus* IFO 1604, *Candida diversa* IFO 1090, *Citeromyces matritensis* IFO 0651, *Debaryomyces Hansenii* IFO 0015, *Hormoascus platypodis* IFO 1471 and the like.

The strains of the above microorganisms have been deposited at IFO (Institute For Fermentation, Osaka, Japan), ATCC (American Type Culture Collection, Rockville, VSA), CBS (Centraalbureau voor Schimmelcultures, Baarn, Netherlands), IAM (Institute of Applied Microbiology, University of Tokyo, Japan) or HUT (Faculty of Engineering, Hiroshima University, Hiroshima, Japan).

These microorganisms can be cultured with any culture medium on which the microorganisms can multiply such as, for instance, culture medium comprising glucose, peptone, yeast extract, meat extract, and the like. The culture of the microorganism is usually carried out under aerobic condition at from 10° to 40° C., preferably from 25° to 35° C., at pH ranging from 3 to 8, preferably from 6 to 7, for 24 to 48 hours.

The asymmetric hydrolysis of ester of indoline-2-carboxylic acid with microorganism can be carried out by adding the substrate, racemic ester [(R,S)-I], to the culture medium when starting culture of the microorganism so that culture of the microorganism and hydrolysis of the racemic ester are conducted simultaneously. Altenatively, it may be carried out by adding racemic ester [(R,S)-I] to the culture medium containing cells which is obtained after culturing the microorganism, or by adding [(R,S)-I] to the cell suspension, wherein cells obtained from centrifugation or filtration after culturing the microorganism are suspended in a buffer solution. In order to achieve better recovering of the product after hydrolysis reaction, the hydrolysis reaction is preferably carried out in such a way that after concentrating the cells by centrifugation, filtration and the like, the cell suspension with a high concentration is prepared, to which racemic ester [(R,S)-I] is added.

Though some of ester [(R,S)-I] has a low solubility in water, this would not disturb the hydrolysis reaction if the reaction is carried out with stirring. In such a case, also an organic solvent such as, for instance, acetone or methanol, or a detergent may be added to the reaction mixture in such an amount that would not interrupt the hydrolysis reaction.

The reaction is carried out at a temperature ranging from 10° to 50° C., preferably from 25° to 35° C., at pH ranging from 5 to 8, preferably from 6.5 to 7.5. Though the reaction time varies depending on a ratio between an amount of the substrate and that of the cells, the reaction may be stopped when a molar ratio of 1:1 between the unreacted ester and the produced carboxylic acid is achieved. However, in view of the activity of the cells in the reaction, an amount of the substrate to be added should be such that the ratio of 1:1 is achieved within 12 to 48 hours. Also since pH value of the reaction mixture is inclined to shift to the acidic side as the hydrolysis reaction proceeds, the pH of the reaction mixture is preferably maintained at from 6 to 7 with a neutralizing agent such as, for instance, NaOH.

As the enzyme from the microorganism, crude enzyme, which is obtained by crushing the cells of the microorganism followed by fractionation with ammonium sulfate or treatment with acetone, or purified enzyme, which is obtained by further purifying the crude enzyme with column chromatography, can be employed. Examples of commercially available enzyme for producing [(R)-II] are, for instance, Bioplase AL-15 (origine: *Bacillus subtilis,* made by Nagase & Company, Ltd.), Protease Amano P (origin: *Aspergillus melleus,* made by Amano Pharmaceutical Co.), Actinase E (origin: *Streptomyces griseus,* made by Kaken Pharmaceutical Co.), Steapsin (derived from hog pancreas, made by Wako Purechemical Industries, Ltd.), Lipase L 3126 (derived from hog pancreas, made by Sigma Chemical Co.), Pancreatic digesting enzyme TA (made by Amano Pharmaceutical Co.) and the like. Examples of commercially available enzyme for producing [(S)-II]

are, for instance, Lipoprotein lipase (L. P. L. Amano 8, origin: *Pseudomonas aeruginosa*, made by Amano Pharmaceutical Co.), Lipase AP-6 (origin: *Aspergillus niger*, made by Amano Pharmaceutical Co.) and the like.

For conducting the asymmetric hydrolysis reaction, the substrate racemic ester [(R,S)-I] is suspended in the reaction mixture with a concentration of 2 to 30% (W/V) and thereto a proper amount of the enzyme is added. The amount of the enzyme is preferably such that, for instance, a ratio of the enzyme to the substrate (by weight) is from 1:5 to 1:1000. Then the reaction is carried out at a temperature ranging from 10° to 40° C., preferably from 25° to 35° C., while an amount of produced carboxylic acid and a decreased amount of ester of carboxylic acid are measured with high performance liquid chromatography, and the reaction is stopped when 1:1 of a molar ratio between [I*] and [II*] in the reaction mixture is obtained. Though the reaction may be carried out at pH value ranging from 4 to 8.5, the pH of the reaction mixture is preferably maintained at from 6 to 7 with a neutralizing agent such as, for instance, NaOH solution since pH value of the reaction mixture is inclined to shift to the acidic side as the hydrolysis reaction proceeds.

After asymmetric hydrolysis with the microorganism or the enzyme, the pH of the reaction mixture is adjusted to 7 and then only optically active ester of indoline-2-carboxylic acid [I*] is extracted with a hydrophobic organic solvent such as ethyl acetate, chloroform, methylene chloride or hexane so that [I*] is separated from hydrophilic optically active indoline-2-carboxylic acid [II*].

Though the thus obtained optically active ester may be concentrated as such to give the ester with a high optical purity, it can be converted into optically active indoline-2-carboxylic acid as follows: i.e. optically active ester of indoline-2-carboxylic acid [(S)-I] or [(R)-I] is hydrolyzed with alkali at room temperature at pH ranging from 9 to 11 for 10 minutes to 2 hours to give [(S)-II] or [(R)-II] respectively. Alternatively, [(S)-I] or [(R)-I] is subjected to the action of the enzymes capable of specifically hydrolyzing [(S)-I] or [(R)-I] such as, for instance, Lipoprotein lipase Amano 3 (made by Amano Pharmaceutical Co.) for [(S)-I] and Steapin (made by Wako Purechemical Industries, Ltd.) for [(R)-I], or to the action of the microorganism capable of specifically hydrolyzing [(S)-I] or [(R)-I] to give [(S)-II] or [(R)-II] respectively.

The pH of the solution obtained after hydrolysis is adjusted to 4 to 6, preferably around 5.0, and the resultant is then extracted with an organic solvent such as methylen chloride, ethyl acetate, toluene or hexane, followed by concentration and crystallization in an organic solvent such as acetone to give [(S)-II] or [(R)-II] with a high optical purity.

On the other hand, optically active indoline-2-carboxylic acid remained in the water layer after extraction of ester of indoline-2-carboxylic acid can also be treated as above, i.e. the pH of the solution is adjusted to 4 to 6, preferably around 5.0, and then the extraction as mentioned above is conducted to give [(R)-II] or [(S)-II] with a high optical purity.

The immobilized enzyme or the immobilized microorganism can be prepared by immobilizing the above-mentioned commercially available enzyme or cells obtained after culturing the microorganism as such on a hydrophobic resin. Alternatively, the cells is crushed and then fractionation with ammonium sulfate or treatment with acetone is carried out to give a crude enzyme, which is immobilized on a hydrophobic resin as such or after further purification.

Various hydrophobic supports may be employed in the present invention as the support for immobilizing the enzyme. The hydrophobic support employed in the present invention does not absorb hydrophilic compound [II*] produced in the asymmetric hydrolysis reaction in water or a buffer solution but adsorb the unreacted ester [I*] through hydrophobic interaction and preferably has a stability even in an alkaline range of pH 8 to 10. Examples of such support are, for instance, a hydrophobic synthetic resin, a hydrophobic resin for chromatography, hydrophobic photo induced crosslinked-resin, hydrophobic urethan prepolymer, a macromolecule material in which a hydrophobic group is introduced by a chemical bonding, and the like.

Immobilization of the enzyme on such support can be carried out by various known methods such as physical adsorption, covalent bonding, ionic bonding, cross-linking and entrapping methods. In case of immobilization of the microorganism, entrapping method and the like may be employed (edited by Fukui, Chibata and Suzuki, "Kosokogaku", P 157–243, Kodansha, 1981; edited by Ichiro Chibata, "Koteikakoso", Kodansha, 1975).

In the industrial process, the immobilized enzyme is preferably prepared by allowing the enzyme to be physically adsorbed on a hydrophobic synthetic adsorbent while the immobilized microorganism is preferably prepared by entrapping the cells in hydrophobic photo induced crosslinked-resin or urethane prepolymer resin in view of simplicity of the process, mechanical strength of the support and economical reason.

Though an amount of the enzyme or microorganism immobilized on the support cannot be sweepingly determined since it various depending on a immobilizing capacity of the support, the amount of the enzyme immobilized on the support may be about 0.1 to about 100 mg, usually about 1 to 20 mg per 1 g wet weight of the support while the amount of the cells immobilized on the support may be 0.1 to 1 g, usually about 0.15 to about 0.5 g per 1 g wet weight of the support.

Though an amount of the substrate which can be loaded on a column filled with the immobilized enzyme or the immobilized microorganism varies depending on a kind of the immobilizing support and that of the substrate ester, the substrate can be loaded on a column in the highest amount as far as the unreacted substrate is not eluted while the substrate is loaded or when a buffer solution is passed through a column. For example, when the immobilized enzyme, wherein the support is a synthetic absorbent Amberlite XAD-7, is filled in a column and the substrate is ester with ethylene glycol, up to 1/5 amount of the substrate based on the column volume can be loaded. For loading the substrate, the substrate is merely placed on the upper part of the column and thereto a buffer solution is added in a column process, or the substrate is mixed with the immobilized enzyme or the immobilized microorganism in a batch process.

The asymmetric hydrolysis reaction of the present invention can be conducted usually at a temperature ranging from 10° to 60° C., preferably from 20° to 40° C. The reaction of the present invention can be carried out at pH ranging from 4.5 to 10, preferably from 6 to 7.5 to give the maximum reaction rate. Since the pH value of the reaction mixture is lowered by indoline-2-carboxylic acid which is produced as the reaction proceeds, the pH is preferably maintained in a fixed range with a buffer solution and the like when a large amount of the substrate is loaded. Buffer solutions of both inorganic acid salt and organic acid salt can be employed for this purpose.

The unreacted ester adsorbed on the immobilizing support for the immobilized enzyme or the immobilized microorganism can be hydrolyzed with alkali at such a pH that does not inactivate the activity of the immobilized enzyme or the immobilized microorganism and can hydrolyze the ester. Though such pH value varies depending on a kind of the enzyme or that of the microorganism, the hydrolysis with alkali is usually carried out at pH 8 to 10.

When the reaction of the present invention is carried out in a column process, a buffer solution is preferably employed in order to maintain the pH value in the system. The immobilized enzyme or the immobilized microorganism is filled in a column and thereto a buffer solution at pH 7.0 is added. Then the substrate ester [(R,S)-I] is loaded and thereto the buffer solution is further added to conduct the asymmetric hydrolysis reaction. The produced hydrophilic compound [II*] is dissolved in the buffer solution and then eluted from the column. The fraction of the eluted buffer solution is analyzed with a high performance liquid chromatography (Finepak SIL $C_{18}$, developing solvent: acetonitrile/water=15/1 (v/v), detector: UV 215 nm). When the compound [II*] can scarecely be detected, a buffer solution at pH 8 to 10 in place of the buffer solution at pH 7.0 is added to hydrolyze the unreacted ester [I*] which is adsorbed on the immobilized enzyme or the immobilized microorganism in the column. The produced compound [II*] having an opposite optical rotation based on the previously obtained hydrophilic compound [II*] is desorbed from the immobilized enzyme or from the immobilized microorganism and then eluted. The fraction of this buffer solution is subjected to the high performance liquid chromatography as above. When the compound [II*] can scarcely be detected in the fraction, the buffer solution at pH 7.0 in place of the buffer solution at pH 8 to 10 is added to the column and again the substrate ester [(R,S)-I] is loaded. By repeating the above-mentioned processes, it is possible to consecutively conduct the asymmetric hydrolysis of the compound [(R,S)-I], separation of the reaction product and hydrolysis with alkali.

When the asymmetric hydrolysis reaction of the racemic compound [(R,S)-I] is carried out in a batch process using the immobilized enzyme or the immobilized microorganism, a water layer containing hydrophilic optically active compound [II*] and the immobilized enzyme or the immobilized microorganism, to which the unreacted hydrophobic optically active compound [I*] is adsorbed, are separated from each other by filtration or moderate centrifugation. The ester adsorbed on the immobilized enzyme or the immobilized microorganism is hydrolyzed with an alkaline solution, which is adjusted to pH 8 to 10 in order not to inactivate the immobilized enzyme or the immobilized microorganism, or with a buffer solution at pH 8 to 10. The hydrolyzed product is desorbed from the immobilized enzyme or the immobilized microorganism to give the optically active compound [II*] having an opposite optical rotation based on the previously obtained [II*]. The immobilized enzyme or the immobilized microorganism can be reused in the reaction.

The pH of the obtained fraction containing indoline-2-carboxylic acid is adjusted to around 5.0 and then concentration, crystallization, precipitation and filtration are successively carried out to give indoline-2-carboxylic acid. Alternatively, after saturating the obtained fraction with ammonium sulfate, the pH of the fraction is adjusted to around 5.0 and extraction with an organic solvent such as ethyl acetate or methylene chloride is carried out, followed by concentration to give indoline-2-carboxylic acid. If necessary, crystallization in an organic solvent such as acetone may further be carried out.

The present invention is more particularly described by the following Examples. However, it should be understood that the present invention is not limited to the Examples and various changes and modifications can be made without departing from the scope and spirit of the present invention.

EXAMPLE 1

[Synthesis of the substrate]

(1) Preparation of (R,S)-amyl-indoline-2-carboxylate [(R,S,)-Ia]

To a solution of 50 g of (R,S,)-indoline-2-carboxyic acid [(R,S)-II] dissolved in 500 ml of amyl alcohol was added 100 ml of concentrated hydrochloric acid and a condensation reaction was conducted at 95° to 100° C. for 3 hours. After completion of the reaction, the reaction mixture was cooled and then the pH thereof was adjusted to 7.0 with 10% sodium hydroxide. Excessive amyl alcohol and water were removed by concentration under reduced pressure. In the concentrated liquid were contained desired (R,S)-amyl-indoline-2-carboxylate [(R,S)-I] and an inorganic salt. To the concentrated liquid was added 1 l of ethyl acetate and the resultant was washed twice with a saturated solution of sodium bicarbonate (200 ml×2), followed by concentration of the ethyl acetate layer to give 60.8 g of [(R,S)-Ia] (yield: 85%).

(2) Preparation of (R,S)-butyl-indoline-2-carboxylate [(R,S)-Ib]

To a mixture of 50 g of (R,S)-indoline-2-carboxylic acid [II] and 250 g of butyl alcohol was added 20 ml of concentrated sulfuric acid and a condensation reaction was conducted at 95° to 100° C. for 3 hours. After completion of the reaction, the reaction mixture was cooled and then the pH thereof was adjusted to 7.0 by adding sodium bicarbonate and a saturated solution of sodium bicarbonate. The resultant was extracted three times with ethyl acetate (500 ml×3) and an ethyl acetate layer was washed with 100 ml of water, followed by dehydration with anhydrous sodium sulfate and further concentration under reduced pressure to give 53.8 g of [(R,S)-Ib] (yield: 80%).

The procedure as above was repeated employing 50 g of (R,S)-indoline-2-carboxylic acid and five equivalents of alcohol based on the acid to give the following substrates:

(R,S)-ethyl-indoline-2-carboxylate [(R,S)-Ic] (49.3 g, yield: 84%)

(R,S)-ethyleneglycol-indoline-2-carboxylate [(R,S)-Id] (50.2 g, yield: 79.0%)

(R,S)-glycerolα-monochlorohydrin-indoline-2-carboxylate [(R,S)-Ie] (45.4 g, yield: 58.0%)

(R,S)-glycerol-indoline-2-carboxylate [(R,S)-If] (57.7 g, yield: 79%)

(R,S)-cyclohexanol-indoline-2-carboxylate [(R,S)-Ig] (52.3 g, yield: 69%)

(R,S)-benzyl alcohol-indoline-2-carboxylate [(R,S)-Ih] (49.7 g, yield: 64.0%)
(R,S)-pentanetriol-indoline-2-carboxylate [(R,S)-Ii] (59.5 g, yield: 73.3%)
(R,S)-dichloropropanol-indoline-2-carboxylate [(R,S)-Ij] (28.1 g, yield: 33.4%)
(R,S)-cyclohexanediol-indoline-2-carboxylate [(R,S)-Ik] (56.4 g, yield: 70.3%)

In a purification process of [(R,S)-Id], [(R,S)-Ie], [(R,S)-Ij], [(R,S)-Ik] and [(R,S)-Ih], methylene chloride was employed as an extraction solvent in place of ethyl acetate.

EXAMPLE 2

To 100 ml of 0.1M phosphate buffer (pH 7.0) were added 1.0 g of Steapsin and 10 g of the substrate (R,S)-amyl-indoline-2-carboxylate [(R,S)-Ia]:

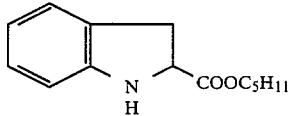

and the asymmetric hydrolysis reaction was carried out with stirring at 30° C. for 24 hours while adjusting to pH 7.0. The reaction mixture was extracted with 100 ml of hexane twice and the hexane layer was dehydrated with anhydrous sodium sulfate, followed by concentration under reduced pressure to give 4.7 g (yield from [(R,S)-Ia]: 94%) of syrup [(S)-Ia] having a specific rotatory power $[\alpha]_D^{25} +5.8°$ (c=1.0, ethanol).

$^1$H NMR (90 MHz)(CDCl$_3$) δ ppm: 0.8 to 1.8 (9H, m, CH$_3$CH$_2$CH$_2$CH$_2$—), 3.2 to 3.45 (2H, d, —CH$_2$O—), 4.0 to 4.4 (4H) and 6.45 to 7.05 (4H, m, Ar—)

To 25 ml of 1N NaOH solution was added 4.7 g of the obtained [(S)-Ia] and the hydrolysis reaction was conducted at room temperature for about 3 hours. After the pH of the reaction mixture was adjusted to 5.0 with 1N hydrochloric acid, the resultant was extracted with 50 ml of ethyl acetate four times, followed by dehydration with anhydrous sodium sulfate, concentration under reduced pressure and recrystallization in acetone-hexane (5 ml −1 ml) to give 24.5 g (yield from [(R,S)-I]: 69%) of (S)-indoline-2-carboxylic acid [(S)-II] as a white powder having a specific rotatory power $[\alpha]_D^{25} +32.4°$ (c=1.0, dimethylformamide (hereinafter referred to as "DMFA"))(the value described in the literature J. Med. Chem., 26, 394 (1983) is $[\alpha]_D^{25} +34.5°$ (c=1.0, DMFA)).

$^1$H NMR (90 MHz)(DMSO-d6) δ ppm: 2.85 to 3.45 (2H), 4.10 to 4.35 (1H, 6.40 to 7.05 (4H, m, Aryl) and 7.2 to 9.0 (2H, broad)

On the other hand, the pH of the water layer after extraction with hexane was adjusted to 5.0 with 1N hydrochloric acid and the resultant was extracted with 100 ml of ethyl acetate four times, followed by work-up as in the case of [(S)-II] to give 2.6 g (yield from [(R,S)-Ia]: 74%) of [(R)-II] having a specific rotatory power $[\alpha]_D^{25} -33.1°$ (c=1.0, DMFA).

EXAMPLES 3 TO 9

The procedure as in Example 1 was repeated except that different substrates and different enzymes were employed. The results are shown in Table 1.

In Examples 3, 4, 5, 8 and 9, the ester of (R)-form was asymmetrically hydrolyzed while in Examples 6 and 7, the ester of (S)-form was asymmetrically hydrolyzed.

$^1$H NMR (90 MHz) data of the substrate (R,S)-butyl-indoline-2-carboxylate [(R,S)-Ib] in Example 8 were as follows:

$^1$H NMR (CDCl$_3$) δ ppm: 0.8 to 1.8 (7H, m, CH$_3$CH$_2$CH$_2$CH$_2$—), 3.25 to 3.4 (2H, d, —CH$_2$O—), 4.05 to 4.45 (4H) and 6.55 to 7.1 (4H, m, Ar—)

$^1$H NMR (90 MHz) data of the substrate (R,S)-ethyl-indoline-2-carboxylate [(R,S)-Ic] in Example 9 were as follows:

$^1$H NMR (CDCl$_3$) δ ppm: 1.1 to 1.4 (3H, t, CH$_3$), 3.2 to 3.4 (2H, d, CH$_3$CH$_2$O—), 4.0 to 4.4 (4H) and 6.55 to 7.1 (4H, m, Ar—)

The reaction condition was as follows:

substrate 10.0 g, enzyme 1.0 g/0.1M phosphate buffer (pH 7.0) 100 ml, 33° C., stirred with stirrer, reacted for 24 hours, adjusted to pH 7.0

TABLE 1

| | | | Product | | | |
|---|---|---|---|---|---|---|
| | | | [(R)-I] Yield (%), $[\alpha]_D^{25}$ (c = 1.0, ethanol) | [(R)-II] Yield (%), $[\alpha]_D^{25}$ (c = 1.0, DMFA) | [(S)-I] Yield (%), $[\alpha]_D^{25}$ (c = 1, ethanol) | [(S)-II] Yield (%), $[\alpha]_D^{25}$ (c = 1.0, DMFA) |
| Ex. | Substrate [(R,S)-I] | Enzyme | | | | |
| 3 | (R,S)—amyl-indoline-2-carboxylate [(R,S)-Ia] | Bioplase AL-15 | — | 49, −33.2° | 94, +4.1° | 70, +25.2° |
| 4 | (R,S)—amyl-indoline-2-carboxylate [(R,S)-Ia] | Protease Amano P | — | 41, −33.8° | 97, +3.6° | 72, +19.8° |
| 5 | (R,S)—amyl-indoline-2-carboxylate [(R,S)-Ia] | Pancreatic digesting enzyme | — | 78, −24.9° | 88, +5.8° | 65, +29.1° |
| 6 | (R,S)—amyl-indoline-2-carboxylate [(R,S)-Ia] | Lipoprotein lipase | 89, −4.9° | 66, −27.4° | — | 71, +22.1° |
| 7 | (R,S)—amyl-indoline-2-carboxylate [(R,S)-Ia] | Lipase AP-6 | 78, −4.8° | 58, −26.1° | — | 84, +15.7° |
| 8 | (R,S)—butyl-indoline-2-carboxylate [(R,S)-Ib] | Steapsin | — | 83, −33.4° | 91, +6.1° | 68, +32.9° |
| 9 | (R,S)—ethyl-indoline-2-carboxylate [(R,S)-Ic] | Steapsin | — | 72, −32.4° | 86, +4.9° | 62, +80.8° |

EXAMPLE 10

A liquid medium having the composition: glucose 4%, yeast extract 0.3%, meat extract 0.3%, peptone 0.3%, ammonium secondary phosphate 0.2% and potassium primary phosphate 0.1% (pH 6.8) was prepared. Each 2 l Sakaguchi flask was charged with 400 ml of the liquid medium and sterilized at 120° C. for 15 minutes.

The above liquid medium was inoculated 10 ml of a liquid medium containing *Pseudomonas aeruginosa* IFO 3080 precultured on a liquid medium of the above composition and the resultant was shaked at 30° C. for 24 hours. Five cultures were obtained and the culture liquid made a total of 2 l. The culture liquid was centrifuged to collect the cells. The cells were suspended in 200 ml of 0.1M phosphate buffer (pH 7.0) and thereto 2.0 g of the substrate (R,S)-amyl-indoline-2-carboxylate [(R,S)-Ia] was added. The reaction was conducted in a 500 ml vessel with stirring at 30° C. for 18 hours while adjusting to pH 7.0 with 1N NaOH solution. After completion of the reaction, a supernatant obtained by centrifugation was extracted with 200 ml of hexane four times, followed by work-up as in Example 1 to give the results as shown in Table 2.

EXAMPLES 11 TO 14

*Pseudomonas aeruginosa* IFO 13130 in Example 11 and *Bacillus subtilis* in Example 13 were cultured as in Example 10. The microorganisms of the genus Aspergillus in Examples 12 and 14 were cultured as in Example 10 except that the composition of the liquid medium was glucose 3.0%, polypeptone 1.0%, yeast extract 0.5%, ammonium secondary phosphate 0.2%, potassium primary phosphate 0.1% (pH 6.5) and a temperature was 28° C.

After culturing the microorganisms, the cells were collected by centrifugation in case of *Pseudomonas aeruginosa* and *Bacillus subtilis*, by filtration in case of the microorganisms of the genus Aspergillus. The collected cells were suspended in 0.1M phosphate buffer at pH 7.0 and then asymmetric hydrolysis by the microorganism, extraction and purification were carried out as in Example 10. The results are shown in Table 2.

The reaction condition was as follows:
substrate (R,S)-amyl-indoline-2-carboxylate [(R,S)-Ia] 2.0 g, suspension of the cells (0.1M phosphate buffer, pH 7.0) 200 ml, 33° C., reacted for 18 hours, adjusted to pH 7.0 extract of the enzyme. To the extract of the enzyme was added 10 g of the substrate (R,S)-amyl-indoline-2-carboxylate [(R,S)-Ia] and the asymmetric hydrolysis reaction was conducted with stirring at 30° C. for 48 hours while adjusting to pH 7.0 with 1N NaOH solution, followed by extraction and purification as in Example 10 to give 1.9 g of [(R)-II] having a specific rotatory power $[\alpha]_D^{25} -22.4°$ (c=1.0, DMFA) and 4.2 g of [(S)-Ia] having a specific rotatory power $[\alpha]_D^{25} +3.3°$ (c=1.0, ethanol).

EXAMPLE 16

To 100 ml of 0.1M phosphate buffer at pH 7.0 were added 10 g of the substrate (R,S)-glycerol-indoline-2-carboxylate [(R,S)-If]:

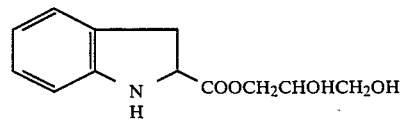

and 0.2 g of Steapsin. The assymmetric hydrolysis reaction was carried out with stirring at 33° C. for 6 hours while adjusting to pH 7.0 with 2N NaOH solution. The reaction mixture was extracted with ethyl acetate three times (200 ml×3) and the ethyl acetate layer was dehydrated with anhydrous sodium sulfate, followed by concentration under reduced pressure to give 4.6 g (yield from [(R,S)-If]: 92%) of viscous syrup [(S)-If] having a specific rotatory power $[\alpha]_D^{25} +15.2°$ (c=1.0, ethanol).

$^1$H NMR (90 MHz)(MeOH d4) δ ppm: 3.2 to 3.45 (2H), 3.5 to 4.7 (9H) and 6.5 to 7.1 (4H, m, Ar—)

To 4.6 g of the obtained [(S)-If] was added 30 ml of 0.1M potassium secondary phosphate and the hydrolysis reaction was carried out at 33° C. for 1 hour while adjusting to pH 10 by dropwise addition of 2N NaOH. Then the pH of the reaction mixture was adjusted to 5.0 with 1N hydrochloric acid and the resultant was extracted with ethyl acetate three times (100 ml×3), followed by dehydration with andhydrous sodium sulfate, concentration under reduced pressure and recrystallization in acetone-hexane (5 ml-1 ml) to give 2.61 g (yield from [(R,S)-If]: 76%) of a white powder of (S)-indoline-2-carboxylic acid [(S)-II] having a specific rotatory power $[\alpha]_D^{25} +32.5°$ (c=1.0, DMFA)(the value described in the literature J. Med. Chem., 26, 394 (1983) is

TABLE 2

| | | Product | | | |
|---|---|---|---|---|---|
| | | [(R)-Ia] Yield (%), $[\alpha]_D^{25}$ (c = 1.0, ethanol) | [(R)-II] Yield (%), $[\alpha]_D^{25}$ (c = 1.0, DMFA) | [(S)-Ia] Yield (%), $[\alpha]_D^{25}$ (c = 1, ethanol) | [(S)-II] Yield (%), $[\alpha]_D^{25}$ (c = 1.0, DMFA) |
| Ex. | Strain | | | | |
| 10 | *Pseudomonas aeruginosa* | 61, −3.1° | 46, −21.9° | — | 69, +23.4° |
| 11 | " | 56, −2.9° | 41, −19.7° | — | 71, +21.8° |
| 12 | *Aspergillus niger* | 68, −2.5° | 47, −17.3° | — | 66, +21.4° |
| 13 | *Bacillus subtilis* | — | 57, −24.2° | 62, +3.9° | 46, +28.3° |
| 14 | *Aspergillus melleus* | — | 59, −23.1° | 59, +3.7° | 43, +26.9° |

EXAMPLE 15

Employing *Pseudomonas aeruginosa* IFO 3080, 2 l of the culture liquid was prepared as in Example 10 and was centrifuged to collect the cells. The collected cells were suspended in 200 ml of 0.1M phosphate buffer (pH 7.0) and were crushed with Brawn homogenizer with cooling, followed by centrifugation to give a cell-free $[\alpha]_D^{25} +34.5°$).

$^1$H NMR (90 MHz)(DMSO-d6) δ ppm: 2.85 to 3.45 (2H), 4.10 to 4.35 (1H) and 6.40 to 7.05 (4H, m, Aryl)

On the other hand, the pH of the water layer remained after the first extraction with ethyl acetate was adjusted to 5.0 with 1N hydrochloric acid and the resultant was extracted with ethyl acetate three times (200 ml×3), followed by work-up as in the case of [(S)-II] to give 3.02 g (yield from [(R,S)-If]: 88%) of [(R)-II] having a specific rotatory power $[\alpha]_D^{25} -29.2°$ (c=1.0, DMFA).

EXAMPLES 17 TO 23

The procedure as in Example 16 was repeated except that different enzymes were employed. The results are shown in Table 3.

In Examples 17, 18, 19, 20 and 21, the ester of (R)-form was asymmetrically hydrolyzed while in Examples 22 and 23, the ester of (S)-form was asymmetrically hydrolyzed.

The reaction condition was as follows: substrate [(R,S)-If] 10 g, enzyme 0.5 g, 0.1M phosphate buffer (pH 7.0) 100 ml, 33° C., stirred with stirrer, reacted for 6 hours, adjusted to pH 7.0 sium primary phosphate 0.1% (pH 6.8) was prepared. Each 2 l Sakaguchi flask was charged with 400 ml of the liquid medium and sterilized at 120° C. for 15 minutes.

To the above liquid medium was inoculated 10 ml of a luquid medium containing *Pseudomonas aeruginosa* IFO 3080 precultured on a liquid medium of the above composition and the resultant was shaked at 30° C. for 24 hours. Five cultures were obtained and the culture liquid made a total of 2 l. The culture liquid was centrifuged to collect the cells. The cells were suspended in 200 ml of 0.1M phosphate buffer (pH 7.0) and thereto 2.0 g of the substrate (R,S)-glycerol-indoline-2-carboxylate [(R,S)-If] was added. The reaction was conducted in a 500 ml vessel with stirring at 30° C. for 18 hours while adjusting to pH 7.0 with 1N NaOH solution. After completion of the reaction, a supernatant obtained by centrifugation was extracted with 200 ml of hexane four times, followed by work-up as in Example 16 to give the results as shown in Table 5.

TABLE 3

| | | Product | | | |
|---|---|---|---|---|---|
| | | [(R)-If] Yield (%), $[\alpha]_D^{25}$ (c = 1.0, ethanol) | [(R)-II] Yield (%), $[\alpha]_D^{25}$ (c = 1.0, DMFA) | [(S)-If] Yield (%), $[\alpha]_D^{25}$ (c = 1.0, ethanol) | [(S)-II] Yield (%), $[\alpha]_D^{25}$ (c = 1.0, DMFA) |
| Ex. | Enzyme | | | | |
| 17 | Actinase E | — | 58, −23.5° | 80, +12.6° | 67, +30.1° |
| 18 | Bioplase | — | 51, −29.6° | 91, +10.3° | 73, +25.4° |
| 19 | Protease Amano P | — | 43, −30.2° | 96, +9.1° | 77, +19.8° |
| 20 | Pancreatic digesting enzyme TA | — | 75, −24.5° | 77, +11.4° | 69, +29.7° |
| 21 | Lipase L3126 | — | 74, −21.4° | 76, +14.0° | 64, +33.2° |
| 22 | Lipoprotein lipase | 82, −10.4° | 64, −26.1° | — | 73, +22.9° |
| 23 | Lipase AP-6 | 78, −9.8° | 59, −26.7° | — | 79, +23.8° |

EXAMPLES 24 TO 29

The procedure as in Example 16 was repeated except that the enzyme is Steapsin and the substrates are esters of (R,S)-indoline-2-carboxylic acid with ethylene glycol [(R,S)-Id], glycerol-α-monochlorohydrin [(R,S)-Ie], 2,3-dichloro-1-propanol [(R,S)-Ij], 1,3,5-pentanetriol [(R,S)-Ii], 1,4-cyclohexanediol [(R,S)-Ik] and benzyl alcohol [(R,S)-Ih]. The results are shown in Table 4.

The reaction condition was as follows:

substrate 10 g, Steapsin 0.5 g, 0.1M phosphate buffer (pH 7.0) 100 ml, 33° C., stirred with stirrer, reacted for 6 hours, adjusted to pH 7.0

EXAMPLES 31 TO 35

*Pseudomonas aeruginosa* IFO 13130 in Example 31 and *Bacillus subtilis* in Example 33 were cultured as in Example 30. The microorganisms of the genus Aspergillus in Examples 32 and 34 were cultured as in Example 30 except that the composition of the liquid medium was glucose 3.0%, polypeptone 1.0%, yeast extract 0.5%, ammonium secondary phosphate 0.2%, potassium primary phosphate 0.1% (pH 6.5) and a temperature was 28° C.

After culturing the microorganisms, the cells were

TABLE 4

| Ex. | Substrate ester of (R,S)-indoline-2-carboxylic acid [(R,S)—I] | Product | | |
|---|---|---|---|---|
| | | [(R)-II] Yield (%), $[\alpha]_D^{25}$ (c = 1.0, DMFA) | [(S)-I] Yield (%), $[\alpha]_D^{25}$ (c = 1.0, ethanol) | [(S)-II] Yield (%), $[\alpha]_D^{25}$ (c = 1, DMFA) |
| 24 | Ester with ethylene glycol [(R,S)-Id] | 86, −22.7° | 72, +17.1° | 57, +34.2° |
| 25 | Ester with glycerol-α-monochlorohydrin [(R,S)-Ie] | 53, −24.2° | 90, +13.8° | 51, +31.2° |
| 26 | Ester with 2,3-dichloro-propanol [(R,S)-Ij] | 48, −25.5° | 88, +10.2° | 43, +29.8° |
| 27 | Ester with 1,3,5-pentanetriol [(R,S)-Ii] | 61, −20.7° | 81, +8.9° | 39, +27.1° |
| 28 | Ester with 1,4-cyclohexane-diol [(R,S)-Ik] | 71, −23.6° | 75, +4.8° | 59, +24.2° |
| 29 | Ester with benzyl alcohol [(R,S)-Ih] | 42, −24.9° | 20, +3.4° | 61, +18.7° |

EXAMPLE 30

A liquid medium having the composition: glucose 4%, yeast extract 0.3%, meat extract 0.3%, peptone 0.3%, ammonium secondary phosphate 0.2% and potascollected by centrifugation in case of *Pseudomonas aeruginosa* and *Bacillus subtilis*, by filtration in case of the microorganisms of the genus Aspergillus. The collected cells were suspended in 0.1M phosphate buffer at pH 7.0 and then asymmetric hydrolysis by the microorganism, extraction and purification were carried out as in Example 30. The results are shown in Table 5.

The reaction condition was as follows:
substrate  (R,S)-glycerol-indoline-2-carboxylate [(R,S)-If] 2.0 g, suspension of the cells (0.1M phosphate buffer, pH 7.0) 200 ml, 33° C., reacted for 18 hours, adjusted to pH 7.0 lowed by dehydration with anhydrous sodium sulfate, concentration under reduced pressure and recrystallization in acetone-hexane (5 ml-1 ml) to give 1.39 g (yield from [(R,S)-If]: 67%) of a white powder (S)-indoline-2-carboxylic acid [(S)-II] having a specific rotatory power $[\alpha]_D^{25}+34.5°$ (c=1.0, DMFA)(the value described in the literature J. Med. Chem., 26, 394 (1983) is $[\alpha]_D^{25}+34.5°$).

TABLE 5

| | | Product | | | |
|---|---|---|---|---|---|
| | | [(R)-If] Yield (%), $[\alpha]_D^{25}$ (c = 1.0, ethanol) | [(R)-II] Yield (%), $[\alpha]_D^{25}$ (c = 1.0, DMFA) | [(S)-If] Yield (%), $[\alpha]_D^{25}$ (c = 1.0, ethanol) | [(S)-II] Yield (%), $[\alpha]_D^{25}$ (c = 1.0, DMFA) |
| Ex. | Strain | | | | |
| 30 | Pseudomonas aeruginosa IFO 3080 | 63, −10.4° | 47, −25.7° | — | 67, +23.2° |
| 31 | Pseudomonas aeruginosa IFO 18130 | 67, −9.7° | 50, −20.8° | — | 69, +19.7° |
| 32 | Aspergillus niger IFO 4407 | 69, −9.1° | 51, −19.2° | — | 65, +20.6° |
| 33 | Bacillus subtilis IFO 3018 | — | 64, −24.8° | 68, +11.1° | 52, +26.8° |
| 34 | Aspergillus melleus IFO 4420 | — | 61, −23.1° | 70, +9.8° | 57, +20.7° |
| 35 | Streptomyces griseus IFO 8358 | — | 72, −24.3° | 67, +12.5° | 55, +27.2° |

EXAMPLE 36

A liquid medium having the composition: glucose 4%, yeast extract 0.3%, meat extract 0.3%, peptone 0.3%, ammonium secondary phosphate 0.2% and potassium primary phosphate 0.1% (pH 6.8) was prepared. Each 2 l Sakaguchi flask was charged with 400 ml of the liquid medium and sterilized at 120° C. for 15 minutes.

To the above liquid medium was inoculated 10 ml of a liquid medium containing Arthrobacter nicotianea IFO 14234 precultured on a liquid medium of the above composition and the resultant was shaked at 30° C. for 24 hours. Five cultures were obtained and the culture liquid made a total of 2 l. The culture liquid was centrifuged to collect the cells. The cells were suspended in 200 ml of 0.1M phosphate buffer (pH 7.0) and thereto 6.0 g of the substrate (R,S)-glycerol-indoline-2-carboxylate [(R,S)-If] was added. The reaction was conducted in a 500 ml vessel with stirring at 30° C. for 18 hours while adjusting to pH 7.0 with 1N NaOH solution. After completion of the reaction, a supernatant obtained by centrifugation was extracted with ethyl acetate four times (200 m×4) and the ethyl acetate layer was dehydrated with anhydrous sodium sulfate, followed by concentration under reduced pressure to give 2.53 g (yield from [(R,S)-If]: 84%) of a viscous syrup [(S)-If] having a specific rotatory power $[\alpha]_D^{25}+14.2°$ (c=1.0, ethanol).

$^1$H NMR (90 MHz)(MeOH d4) δ ppm: 3.2 to 3.45 (2H), 3.5 to 4.7 (9H) and 6.5 to 7.1 (4H, m, Ar—)

To 2.53 g of the obtained [(S)-If] was added 20 ml of 0.1M potassium secondary phosphate and the hydrolysis reaction was carried out at 33° C. for 1 hour while adjusting to pH 10 by dropwise addition of 2N NaOH. Then the pH of the reaction mixture was adjusted to 5.0 with 1N hydrochloric acid and the resultant was extracted with ethyl acetate three times (100 ml×3), fol- $^1$H NMR (90 MHz)(DMSO-d6) δ ppm: 2.85 to 3.45 (2H), 4.10 to 4.35 (1H) and 6.40 to 7.05 (4H, m, Aryl)

On the other hand, the pH of the water layer remained after the first extraction with ethyl acetate was adjusted to 5.0 with 1N hydrochloric acid and the resultant was extracted with ethyl acetate three times (200 ml×3), followed by work-up as in the case of [(S)-II] to give 1.58 g (yield from [(R,S)-If]: 77%) of [(R)-II] having a specific rotatory power $[\alpha]_D^{25}-24.7°$ (c=1.0, DMFA).

EXAMPLE 37

The asymmetric hydrolysis reaction with microorganism, extraction and purification as in Example 36 were carried out employing the strain Alcaligenes faecalis IFO 12669 and the racemic substrate (R,S)-amyl-indoline-2-carboxylate acid [(R,S)-Ia]. The asymmetric hydrolysis reaction was conducted for 24 hours to give 2.77 g (yield from [(R,S)-Ia]: 92%) of [(R)-Ia] having a specific rotatory power $[\alpha]_D^{25}-5.4°$ (c=1.0, ethanol), which was further hydrolyzed with alkali to give 159 g (yield from [(R,S)-Ia]: 76%) of [(R)-II] having a specific rotatory power $[\alpha]_D^{25}-33.1°$ (c=1.0, DMFA). On the other hand, 1.32 g (yield from [(R,S)-Ia]: 63%) of [(S)-II] was obtained and had a specific rotatory power $[\alpha]_D^{25}+26.8°$ (c=1.0, DMFA).

EXAMPLES 38 TO 47

The procedure as in Example 36 was repeated except that various strains of the microorganism and the racemic substrate (R,S)-ethylene glycol-indoline-2-carboxylate [(R,S)-Id] were employed. The results are shown in Table 6.

In Examples 38, 39, 40, 41 and 42, the ester of (R)-form was asymmetrically hydrolyzed while in Examples 43, 44, 45, 46 and 47, the ester of (S)-form was asymmetrically hydrolyzed.

TABLE 6

| Ex. | Strain | Product | | | |
|---|---|---|---|---|---|
| | | [(R)-Id] Yield (%), $[\alpha]_D^{25}$ (c = 1.0, ethanol) | [(R)-II] Yield (%), $[\alpha]_D^{25}$ (c = 1.0, DMFA) | [(S)-Id] Yield (%), $[\alpha]_D^{25}$ (c = 1.0 ethanol) | [(S)-II] Yield (%), $[\alpha]_D^{25}$ (c = 1.0, DMFA) |
| 38 | Saccharomyces cerevisiae HUT 7018 | — | 78, −24.8° | 86, +16.9° | 69, +30.3° |
| 39 | Aeromonas hydrophila IFO 3820 | — | 73, −26.7° | 89, +17.3° | 70, +31.4° |
| 40 | Acidiphilium cryptum IFO 14242 | — | 81, −23.5° | 83, +18.6° | 64, +33.3° |
| 41 | Brevibacterium protophormiae IFO 12128 | — | 77, −24.1° | 86, +15.9° | 68, +27.9° |
| 42 | Corynebacterium paurometabolum IFO 12160 | — | 82, −21.2° | 80, +15.4° | 65, +25.7° |
| 43 | Nadsonia elongata IFO 0665 | 84, −15.7° | 68, −29.4° | — | 79, +22.5° |
| 44 | Rhodotorula glutinis IAM 4642 | 87, −16.4° | 71, −32.0° | — | 77, +24.1° |
| 45 | Torulopsis gropengiesseri IFO 0659 | 88, −15.5° | 70, −30.7° | — | 80, +23.6° |
| 46 | Protaminobacter alboflavus IFO 3707 | 89, −18.8° | 72, −33.9° | — | 81, +26.2° |
| 47 | Pseudomonas acidovorans IFO 13582 | 72, −19.2° | 60, −34,4° | — | 91, +21.8° |

EXAMPLES 48 TO 67

The culture as in Example 36 was carried out employing various strains of the microorganism, the culture medium having the composition: glucose 3.0%, polypeptone 1.0%, yeast extract 0.5% ammonium secondary phosphate 0.2%, potassium primary phosphate 0.1% (pH 6.5) and a temperature of 28° C.

After culturing the microorganism, the cells were collected by filtration and the collected cells were suspended in 0.1M phosphate buffer at pH 7.0, followed by the asymmetric hydrolysis of (R,S)-glycerol-indoline-2-carboxylate [(R,S)-If], extraction and purification as in Example 36 to give the results as shown in Table 7.

The strains of the microorganism in Examples 48 to 65 hydrolyzed the ester of (S)-form while those in Examples 66 and 67 hydrolyzed the ester of (R)-form.

TABLE 7

| Ex. | Strain | Product | | | |
|---|---|---|---|---|---|
| | | [(R)-If] Yield (%), $[\alpha]_D^{25}$ (c = 1.0, ethanol) | [(R)-II] Yield (%), $[\alpha]_D^{25}$ (c = 1.0, DMFA) | [(S)-If] Yield (%), $[\alpha]_D^{25}$ (c = 1.0 ethanol) | [(S)-II] Yield (%), $[\alpha]_D^{25}$ (c = 1.0, DMFA) |
| 48 | Arthrinium phaeospermum IFO 5703 | 82, −13.3° | 69, −30.2° | — | 80, +23.1° |
| 49 | Aspergillus ficuum IFO 4280 | 85, −12.9° | 74, −28.7° | — | 77, +21.0° |
| 50 | Cephalosporium mycophilum IFO 8580 | 86, −14.2° | 74, −32.9° | — | 75, +28.9° |
| 51 | Echinopodospora jamaicensis IFO 30406 | 78, −13.5° | 68, −31.6° | — | 84, +23.3° |
| 52 | Emericellopsis glabra IFO 9031 | 88, −14.4° | 76, −33.4° | — | 82, +29.7° |
| 53 | Hypocrea lactea IFO 8434 | 86, −12.6° | 72, −27.9° | — | 79, +22.4° |
| 54 | Isaria atypicola IFO 9205 | 90, −12.9° | 79, −28.6° | — | 80, +22.1° |
| 55 | Lepista nuda IFO 8104 | 89, −15.1° | 77, −34.1° | — | 81, +29.9° |
| 56 | Nectria flammea IFO 30306 | 87, −14.1° | 75, −33.0° | — | 74, +27.8° |
| 57 | Phialophora fastigiasta IFO 6850 | 84, −12.7° | 72, −29.2° | — | 79, +21.8° |
| 58 | Pestalotiopsis distincta IFO 9981 | 81, −12.6° | 67, −26.8° | — | 76, +19.7° |
| 59 | Podospora carbonaria IFO 30294 | 77, −11.2° | 62, −23.4° | — | 68, +18.5° |
| 60 | Moniliella tomentosa CBS 22032 | 79, −12.7° | 68, −29.2° | — | 66, +23.9° |
| 61 | Kluyveromyces fragilis IFO 0288 | 84, −9.6° | 75, −20.3° | — | 71, +18.4° |
| 62 | Schzosaccharomyces pombe IFO 0347 | 72, −11.4° | 62, −25.6° | — | 78, +17.1° |
| 63 | Wickerhamia fluorescens IFO 1116 | 70, −9.8° | 57, −20.4° | — | 77, +16.9° |
| 64 | Arthrobacter crystallopoietes IFO 14235 | 77, −7.2° | 64, −17.8° | — | 65, +14.2° |

TABLE 7-continued

|  |  | Product | | | |
|---|---|---|---|---|---|
|  |  | [(R)-If] Yield (%), $[\alpha]_D^{25}$ (c = 1.0, ethanol) | [(R)-II] Yield (%), $[\alpha]_D^{25}$ (c = 1.0, DMFA) | [(S)-If] Yield (%), $[\alpha]_D^{25}$ (c = 1.0 ethanol) | [(S)-II] Yield (%), $[\alpha]_D^{25}$ (c = 1.0, DMFA) |
| Ex. | Strain | | | | |
| 65 | *Brevibacterium flavum* ATCC 21269 | 81, −6.8° | 68, −14.6° | — | 71, +12.7° |
| 66 | *Trichosporon cutaneum* IFO 1200 | — | 62, −23.5° | 78, +12.1° | 69, +28.9° |
| 67 | *Pseudomonas oxalacticus* IFO 13593 | — | 59, −22.4° | 75, +11.2° | 63, +26.5° |

EXAMPLES 68 TO 72

As in Example 36, the culture of the microorganism and the asymmetric hydrolysis reaction were carried out. The results are shown in Table 8.

The strains of the microorganism in every Examples 68 to 72 hydrolyzed the ester of (S)-form.

TABLE 8

| Ex. | Substrate [(R,S)-I] Ester of (R,S)-indoline-2-carboxylic acid | Strain | Product | | |
|---|---|---|---|---|---|
|  |  |  | [(R)-I] Yield (%), $[\alpha]_D^{25}$ (c = 1.0, ethanol) | [(R)-II] Yield (%), $[\alpha]_D^{25}$ (c = 1.0, DMFA) | [(S)-II] Yield (%), $[\alpha]_D^{25}$ (c = 1.0 ethanol) |
| 68 | Ester with glycerol-α-monochlorohydrin [(R,S)-Ie] | *Botryoascus synnaedendrus* IFO 1604 | 87, −13.4° | 53, −31.2° | 57, +25.1° |
| 69 | Ester with 2,3-dichloropropanol [(R,S)-Ij] | *Candida diversa* IFO 1090 | 80, −9.9° | 43, −27.6° | 43, +21.7° |
| 70 | Ester with 1,3,5-pentanetriol [(R,S)-Ii] | *Cyteromyces matriensis* IFO 0651 | 72, −8.8° | 39, −25.7° | 61, +20.8° |
| 71 | Ester with 1,4-cyclohexanediol [(R,S)-Ik] | *Debaryomyces hansenii* IFO 0015 | 76, −4.9° | 62, −23.6° | 59, +20.5° |
| 72 | Ester with benzyl alcohol [(R,S)-Ih] | *Homoascus platypodis* IFO 1471 | 88, −3.7° | 67, −19.2° | 52, +18.4° |

EXAMPLE 73

To 60 ml of 0.1M phosphate buffer at pH 7.0 was added 3 g of Actinase E (derived from *Streptomyces griseus*, made by Kaken Pharmaceutical Co.) and the mixture was filtered to remove insoluble material. To the filtrate was added 60 g wet weight (water content: 71%) of a porous methacrylate adsorbent Amberlite XAD-7 (made by Rohm & Haas Co.) washed with methanol and water and the resultant was slowly stirred at a low temperature (4° C.) for a night so that the enzyme was immobilized on the adsorbent by adsorption. The immobilized enzyme suspension was filtered by suction with glass filter, followed by washing with 0.1M phosphate buffer three times (100 ml×3) and filtration by suction to give wet immobilized enzyme. This immobilized lipase was filled in a column (inner diameter: 2.2 cm, length: 15 cm), to which 5 g of racemic ester (R,S)-ethylene glycol-indoline-2-carboxylate [(R,S)-Id] was loaded while keeping at 33° C. and 0.1M phosphate buffer at pH 7.0 was passed through the column at a flow rate of 20 ml/h. Each 20 ml of a liquid eluted from the column was taken with a fraction collector and subjected to a liquid chromatography analysis. Only hydrophilic indoline-2-carboxylic acid produced by the asymmetric hydrolysis was contained in the fraction of phosphate buffer. 360 ml of the fraction of phosphate buffer was saturated with ammonium sulfate and the resultant was adjusted to pH 5.0, to which an equivalent amount of ethyl acetate was added, followed by extraction of indoline-2-carboxylic acid three times, dehydration, concentration under reduced pressure, recrystallization from acetone-hexane (8 ml-2 ml) and drying in vacuo to give 1.51 g (yield from [(R,S)-Id]: 77%) of (R)-indoline-2-carboxylic acid [(R)-II] having a specific rotatory power $[\alpha]_D^{25} -30.5°$ (c=1.0, DMFA) (the value described in the literature J. Med. Chem., 26, 394 (1983) is $[\alpha]_D^{25}+34.5°$ (c=1.0, DMFA) as a white powder. After passing 400 ml of the phosphate buffer, 0.1M K$_2$HPO$_4$—NaOH solution at pH 10.0 in place of the phosphate buffer was passed through the column at a flow rate of 40 ml/h so as to hydrolyze the unreacted ester (R,S)-ethylene glycolindoline-2-carboxylate [(R,S)-Id] adsorbed on the immobilized enzyme support in the column, and then [II] was desorbed from the support and eluted. After 300 ml of the alkaline buffer fraction containing [II] was adjusted to pH 5.0 with 2N hydrochloric acid, the resultant was extracted with an equivalent amount of ethyl acetate three times, followed by dehydration, concentration under reduced pressure and recrystallization from acetone-hexane (6 ml-1.5 ml) to give 1.34 g (yield from [(R,S)-Id]: 68%) of (S)-indoline-2carboxylic acid [(S)-II] having a specific rotatory power $[\alpha]_D^{25}+32.7°$ (c=1.0, DMFA) as a white powder.

In the above processes employing the buffer solutions at pH 7.0 and at pH 10.0, desorption of the enzyme was not observed.

EXAMPLE 74

After passing 50 ml of 0.1M phosphate buffer at pH 7.0 thorugh the column employed in Example 73 in which immobilized Actinase E is filled, 5 g of racemic ethylene glycol-indoline-2-carboxylate [(R,S)-Id] was loaded on the column and the asymmetric hydrolysis reaction was carried out at pH 7.0, followed by elution of production carboxylic acid, alkaline, hydroylsis of the ester adsorbed on the column, desorption and elution of carboxylic acid. A series of the above reactions and the elution procedures were repeated 10 times and in every course each fraction of the phosphate buffer at pH 7.0 and fraction of the phosphate buffer at pH 10.0 were treated as in Example 73. As the result, each fraction of the phosphate buffer at pH 7.0 gave (R)-indoline-2-carboxylic acid [(R)-II] having a specific rotatory power $[\alpha]_D^{25}$ ranging from $-29.5°$ to $-30.9°$ (c=1.0, DMFA) with a yield ranging from 1.40 to 1.56 g (yield from [(R,S)-Id]: 71 to 79%). Each fraction of the phosphate buffer at pH 10.0 gave (S)-indoline-2-carboxylic acid [(S)-II] having a specific rotatory power $[\alpha]_D^{25}$ ranging from $+30.3°$ to $+32.2°$ (c=1.0, DMFA) with a yield ranging from 1.28 to 1.35 g (yield from [(R,S)-Id]: 65 to 69%).

EXAMPLES 75 TO 80

The procedure of Example 73 was repeated employing different substrate esters and different supports for immobilizing the enzyme to give the results as shown in Table 9. In every Example, 5 g of the substrate was loaded.

TABLE 9

| Ex. | Substrate | Support | Indoline-2-carboxylic acid [II*] | |
|---|---|---|---|---|
| | | | (R)-form | (S)-form |
| | | | $[\alpha]_D^{25}$ (c = 1.0, DMFA), yield (g) | |
| 75 | Monochlorohydrin-indoline-2-carboxylate [(R,S)-Ic] | Amberlite XAD-2 | −25.3°, 1.14 | +30.1°, 1.02 |
| 76 | Butyl-indoline-2-carboxylate [(R,S)-Ib] | Diaion HP 20 | −22.7°, 1.27 | +20.4°, 1.78 |
| 77 | Glycerol-indoline-2-carboxylate [(R,S)-If] | Diaion HP 20 | −28.4°, 1.42 | +31.2°, 1.23 |
| 78 | Cyclohexanol-indoline-2-carboxylate [(R,S)-Ig] | Amberlite XAD-7 | −27.8°, 0.76 | +18.3°, 1.90 |
| 79 | Benzyl alcohol-indoline-2-carboxylate [(R,S)-Ih] | Amberlite XAD-8 | −29.6°, 0.63 | +17.1°, 2.01 |
| 80 | Pentanetriol-indoline-2-carboxylate [(R,S)-Ii] | Amberlite XAD-7 | −27.1°, 1.17 | +26.7°, 1.32 |

Note: Diaion (made by MITSUBISHI CHEMICAL INDUSTRIES LTD.)

EXAMPLES 81 TO 85

The procedure as in Example 73 was repeated employing different enzymes and the substrate ethylene glycol-indoline-2-carboxylate [(R,S)-Id] to give the results as shown in Table 10. In Examples 83 and 84, a buffer at pH 9.0 was employed for hydrolyzing the ester. In Examples 81 to 84, the ester of (R)-form was hydrolyzed while in Example 85, the ester of (S)-form was hydrolyzed.

TABLE 10

| Ex. | Enzyme | Indoline-2-carboxylic acid [II*] | |
|---|---|---|---|
| | | (R)-form | (S)-form |
| | | $[\alpha]_D^{25}$ (c = 1.0, DMFA), yield (g) | |
| 81 | Bioplase AL-15 (*1) | −23.1°, 1.41 | +24.7°, 1.35 |
| 82 | Protease Amano P (*2) | −23.6°, 1.02 | +19.7°, 1.53 |
| 83 | Pancreatic digesting enzyme (*3) | −21.5°, 1.23 | +22.0°, 1.14 |
| 84 | Steapsin Wako Purechemical Industries, Ltd. (*4) | −26.7°, 1.35 | +29.8°, 1.07 |

TABLE 10-continued

| Ex. | Enzyme | Indoline-2-carboxylic acid [II*] | |
|---|---|---|---|
| | | (R)-form | (S)-form |
| | | $[\alpha]_D^{25}$ (c = 1.0, DMFA), yield (g) | |
| 85 | Lipase AP-6 (*5) | −23.9°, 1.38 | +20.4°, 1.47 |

Note:
(*1) origin: *Bacillus subtilis*, made by Nagase & company, Ltd.
(*2) origin: *Aspergillus melleus*, made by Amano Pharmaceutical Co.
(*3) made by Amano Pharmaceutical Co.
(*4) from hog pancrea, made by Wako Purechemical Industries, Ltd.
(*5) origin: *Aspergillus niger*, made by Amano Pharaceutical Co.

EXAMPLE 86

A liquid medium having the composition: glucose 4%, yeast extract 0.3%, meat extract 0.3%, peptone 0.3%, ammonium secondary phosphate 0.2% and potassium primary phosphate 0.1% (pH 6.8) was prepared. Each 2 l Sakaguchi flask was charged with 400 ml of the liquid medium and sterilized at 120° C. for 15 minutes.

To the above liquid medium was inoculated 10 ml of a liquid medium containing *Pseudomonas acidovorans* IFO 13582 precultured on a liquid medium of the above composition and the resultant was shaked at 30° C. for 24 hours. Five cultures were obtained and the culture liquid made a total of 2 l. The culture liquid was centrifuged to collect the cells. In 40 ml of 20 m M phosphate fubber (pH 7.0) 20 g of the wet cells were suspended and thereto 20 g of urethan prepolymer PU-3 (made by Toyo Tire and Rubber Co., Ltd.) was added. The mixture was quickly stirred at 40° C. and then immediately cooled to 4° C. to be allowed to stand for 30 minutes. The thus obtained immobilized microorganism was cut into about 2×2×2 mm and was filled into the column (inner diameter: 2.2 cm, length: 15 cm), which was kept at 33° C. After passing 50 ml of 0.1M phosphate buffer at pH 7.0 through the column, 4 g of the substrate glycerol-indoline-2-carboxylate [(R,S)-If] was loaded. The asymmetric hydrolysis reaction was carried out by passing 0.1M phosphate buffer at pH 7.0 through the column at a flow rate of 15 ml/h and each 20 ml of the eluate was collected from the column with a fraction collector, which was then subjected to a liquid chromatography analysis. In this phosphate buffer fraction, only hydrophilic indoline-2-carboxylic acid was contained. 300 ml of the phosphate buffer fraction was saturated with ammonium sulfate and the pH of the mixture was adjusted to 5.0, followed by extraction of indoline-2-carboxylic acid with an equivalent amount of ethyl acetate three times. The obtained ethyl acetate layer was dehydrated and concentrated under reduced pressure, followed by recrystallization in acetone-hexane (5 ml-1 ml). After dryness in vacuum, 1.05 g of (S)-indoline-2-carboxylic acid [(S)-II] having a specific rotatory power $[\alpha]_D^{25}+23.7°$ (c=1.0, DMFA) was obtained.

After passing 340 ml of the phosphate buffer through the column, 0.1M $K_2HPO_4$—NaOH buffer at pH 9.5 in place of the previous buffer was passed through the column at a flow rate of 40 ml/min to hydrolyze the unreacted ester glycerol-indoline-2-carboxylate [(R)-If] to give (R)-indoline-carboxylic acid [(R)-II], which was desorbed and eluted. 300 ml of the alkaline buffer containing [(R)-II] was treated as in Example 73 to give 0.94 g of (R)-indoline-2-carboxylic acid [(R)-II] having a specific rotatory power $[\alpha]_d^{25}-29.2°$ (c=1.0, DMFA) as a white powder.

EXAMPLES 87 TO 90

The culture, the immobilization, the asymmetric hydrolysis and the separation procedures as in Example 86 were carried out employing different strains of the microorganism to give the results are shown in Table 11. As the substrate, 4 g of [(R,S)-Id] was loaded.

In Examples 87 and 88, the strains of the microorganism hydrolyzed stereo-specifically the ester of (R)-form while in Examples 89 and 90, the strains of the microorganism hydrolyzed the ester of (S)-form.

TABLE 11

| | | Indoline-2-carboxylic acid [II*] | |
|---|---|---|---|
| | | (R)-form | (S)-form |
| | | $[\alpha]_D^{25}$ (c = 1.0, DMFA), yield (g) | |
| Ex. | Strain | | |
| 87 | *Arthrobacter nicotianae* IFO 14234 | −20.7°, 1.26 | +26.9°, 1.09 |
| 88 | *Brevibacterium protophormiae* IFO 12128 | −18.8°, 1.19 | +24.3°, 1.12 |
| 89 | *Alcaligenes faecalis* IFO 12669 | −28.4°, 1.11 | +23.8°, 1.24 |
| 90 | *Pseudomonas acidovorans* IFO 13582 | −27.2°, 0.98 | +21.2°, 1.29 |

EXAMPLE 91

After adding 10 g of lipase (Steapsin made by Wako Purechemical Industries, Ltd.) having (R)-selective esterase activity to 100 ml of 0.1M phosphate buffer at pH 7.0, a mixture was stirred and the insoluble material was removed. To the filtrate was added 60 g wet weight (containing 71% of water) of the methacrylate porous adsorbent Amberlite XAD-7 (made by Rohm & Haas Co.), which was washed with methanol and then with water, and a mixture was slowly stirred in a cold room (4° C.) for a night to immobilize the enzyme on the support by adsorption. The suspension containing the immobilized enzyme was filtered with suction by means of glass filter and the the filtrate was washed with 0.1M phosphate buffer at pH 7.0 three times (100 ml×3), followed by filtration with suction to give the wet immobilized enzyme. The obtained immobilized lipase was filled in the column (inner diameter: 2.2 cm, length: 15 cm), which was kept at 33° C. On the column was loaded 5 g of racemic amyl-indoline-2-carboxylate [(R,S)-Ia] and 0.1M phosphate buffer at pH 7.0 was passed through the column at a flow rate of 6 ml/h. Each 12 ml of the eluate collected from the column by a fraction collector was subjected to a liquid chromatography analysis. Only hydrophilic indoline-2-carboxylic acid produced by the asymmetric hydrolysis was contained. 180 ml of the phosphate buffer fraction was saturated with ammonium sulfate and the pH of the mixture was adjusted to 5.0, followed by extraction of indoline-2-carboxylic acid with an equivalent amount of ethyl acetate three times. The obtained ethyl acetate layer was dehydrated and concentrated under reduced pressure, followed by recrystallization in acetone-hexane (5 ml-1 ml). After driness in vacuum, 1.26 g of (R)-indoline2-carboxylic acid [(R)-II] having a specific rotatory power $[\alpha]_D^{25}-32.5°$ (c=1.0, DMFA) (the value described in the literature J. Med. Chem. 26, 394 (1983) by D. H. Kim et al. is $[\alpha]_D^{25}+34.5°$ (c=0.91, DMFA) was obtained as a white powder.

After passing 180 ml of the phosphate buffer through the column, hexane in place of the phosphate buffer was passed through the column at a flow rate of 1.0 ml/min to elute unreacted hydrophobic amyl-indoline-2-carboxylate adsorbed on the support for the immobilized enzyme in the column. Each 10 ml of the eluate hexane solution was collected by a fraction collector and 90 ml of the fraction containing amyl-indoline-2-carboxylate was concentrated to give 2.38 g of syrup [(S)-Ia] (yield from [(R,S)-Ia]: 95%) having a specific rotatory power $[\alpha]_D^{25}+5.6°$ (c=1.0, ethanol). To 2.38 g of the obtained [(S)-Ia] was added 15 ml of 1N sodium hydroxide and the hydrolysis reaction was carried out at room temperature for about 3 hours. After adjusting the pH of the reaction mixture to 5.0 with 1N hydrochloric acid, extraction was made with ethyl acetate four times (15 ml×4), followed by dehydration with anhydrous sodium sulfate, concentration under reduced pressure and recrystallization in acetone-hexane (5 ml-1 ml) to give 1.23 g (yield from [(R,S)-Ia]: 70%) of (S)-indoline-2-carboxylic acid [(S)-II] having a specific rotatory power $[\alpha]_D^{25}+33.9°$ (c=1.0, DMFA) as a white powder. In the above elution procedures with the phosphate buffer and with hexane, the desorption of the enzyme was not observed.

EXAMPLE 92

After passing 50 ml of 0.1M phosphate buffer at pH 7.0 through the column employed in Example 91 in which immobilized Steapsin is filled, 5 g of racemic amyl-indoline-2-carboxylate [(R,S)-Ia] was loaded on the column, followed by the hydrolysis reaction with the phosphate buffer, elution of produced carboxylic acid and elution of the unreacted ester with hexane as in Example 91. A series of the above reactions and the elution procedures were repeated 20 times and in every course each fraction of the phosphate buffer and fraction of the hexane eluate were treated as in Example 91. As the result, each fraction of the phosphate buffer gave (R)-indoline-2-carboxylic acid [(R)-II] having a specific rotatory power $[\alpha]_D^{25}$ ranging from 31.9° to 33.1° (c=1.0, DMFA) with a yield ranging from 1.21 to 1.27 g (yield from [(R,S)-Ia]: 69 to 73%). Each fraction of the hexane eluate gave (S)-indoline-2-carboxylic acid [(S)-II] having a specific rotatory power $[\alpha]_D^{25}$ ranging from +32.2° to +34.1° (c=1.0, DMFA) with a yield ranging from 1.18 to 1.24 g (yield from [(R,S)-Ia]: 68 to 71 %).

EXAMPLE 93

Lipoprotein lipase Amano 3 (LPL) having (S)-selective esterase activity in place of Steapsin was immobilized on Amberlite XAD-7 as in Example 91. The immobilized LPL was filled in the column (inner diameter:

2.2 cm, length: 15 cm), followed by work-up as in Examples 91 and 92. The asymmetric hydrolysis of amyl-indoline-2-carboxylate [(R,S)-Ia] and the separation of the product were repeated 10 times. As the result, each phosphate buffer fraction gave (S)-indoline-2-carboxylic acid [(S)-II] having a specific rotatory power $[\alpha]_D^{25}$ ranging from +19.8° to +22.3° (c=1.0, DMFA) with a yield ranging from 1.26 to 1.32 g (yield from [(R,S)-Ia]: 72 to 76%). Each fraction of the hexane eluate give (R)-indoline-2-carboxylic acid [(R)-II] having a specific rotatory power $[\alpha]_D^{25}$ ranging from −25.1° to −27.5° (c=1.0, DMFA) with a yield ranging from 1.03 to 1.11 g (yield from [(R,S)-Ia]: 59 to 64%).

EXAMPLES 94 TO 97

The procedure as in Example 91 was repeated employing different enzymes and substrates to give the results as shown in Table 12. In every Example, 5 g of the substrate was loaded.

TABLE 12

| | | | Indoline-2-carboxylic acid [II*] | |
|---|---|---|---|---|
| | | | (R)-form | (S)-form |
| Ex. | Enzyme | Substrate specificity | Substrate | $[\alpha]_D^{25}$ (c = 1.0, DMFA), yield (g) | |
| 94 | Bioplase AL-15 | (R) | Butyl-indoline-2-carboxylate [(R,S)-Ib] | −33.2°, 1.17 | +25.4°, 1.48 |
| 95 | Protease Amano P | (R) | Butyl-indoline-2-carboxylate [(R,S)-Ib] | −33.5°, 1.03 | +19.7°, 1.51 |
| 96 | Lipase AP-6 | (S) | Amyl-indoline-2-carboxylate [(R,S)-Ia] | −22.1°, 1.22 | +26.6°, 1.39 |
| 97 | Pancreatic digesting enzyme | (R) | Amyl-indoline-2-carboxylate [(R,S)-Ia] | −29.1°, 1.41 | +29.1°, 1.05 |

EXAMPLE 98

Immobilized lipase (Steapsin) was prepared as in Example 91 employing synthetic adsorbent Diaion HP 2MG (made by MITSUBISHI CHEMICAL INDUSTRIES LTD.) in place of Amberlite XAD-7. The immobilized lipase was filled in the column (inner diameter: 2.2 cm, length: 15 cm) and 5 g of amyl-indoline-2-carboxylate [(R,S)-Ia] was loaded on the column, followed by asymmetric hydrolysis and separation of the product as in Example 91. As the result, the fraction of the phosphate buffer gave 1.25 g of (R)-indoline-2-carboxylic acid [(R)-II] having a specific rotatory power $[\alpha]_D^{25}-32.7°$ (c=1.0, DMFA) while the fraction of the hexane eluate gave 1.17 g of (S)-indoline-2-carboxylic acid [(S)-II] having a specific rotatory power $[\alpha]_D^{25}+33.5°$ (c=1.0, DMFA)

EXAMPLE 99

A liquid medium having the composition: glucose 4%, yeast extract 0.3%, meat extract 0.3%, peptone 0.3%, ammonium secondary phosphate 0.2% and potassium primary phosphate 0.1% (pH 6.8) was prepared. Each 2 l Sakaguchi flask was charged with 400 ml of the liquid medium and sterilized at 120° C. for 15 minutes.

To the above liquid medium was inoculated 10 ml of a liquid medium containing *Pseudomonas aeruginosa* IFO 3080 precultured on a liquid medium of the above composition and the resultant was shaked at 30° C. for 24 hours. Five cultures were obtained and the culture liquid made a total of 2 l. The culture liquid was centrifuged to collect the cells. In 40 ml of 20m M phosphate buffer (pH 7.0) was suspended 20 g of the wet cells and thereto 20 g of urethan prepolymer PU-3 (made by Toyo Tire and Rubber Co., Ltd.) was added. The mixture was quickly stirred at 40° C. and then cooled to 4° C. to be allowed to stand for 30 minutes. The thus obtained immobilized microorganism was cut into about 2×2×2 mm and was filled in the column (inner diameter: 2.2 cm, length: 15 cm), which was kept at 33° C. After passing 50 ml of 0.1M phosphate buffer at pH 7.0 through the column, 4 g of the substrate amyl-indoline-2-carboxylate [(R,S)-Ia] was loaded. The asymmetric hydrolysis reaction was carried out by passing 0.1M phosphate buffer at pH 7.0 through the column at a flow rate of 4 ml/h and each 12 ml of the eluate was collected from the column with a fraction collector, which was then subjected to a liquid chromatography analysis. In this fraction, only hydrophilic indoline-2-carboxylic acid produced was contained. 180 ml of the phosphate buffer fraction was saturated with ammonium sulfate and the pH of the mixture was adjusted to 5.0, followed by extraction of indoline-2-carboxylic acid with an equivalent amount of ethyl acetate three times. The obtained ethyl acetate layer was dehydrated and concentrated under reduced pressure, followed by recrystallization in acetone-hexane (5 ml–1 ml). After dryness in vacuum, 0.89 g of (S)-indoline-2-carboxylic acid [(S)-II] having a specific rotatory power $[\alpha]_D^{25}+23.7°$ (c=1.0, DMFA) was obtained.

After passing 180 ml of the phosphate buffer through the column, hexane in place of the phosphate buffer was passed through the column at a flow rate of 1.0 ml/min to elute amyl-indoline-2-carboxylate [(R)-Ia] adsorbed on the immobilized enzyme support in the column. Each 10 ml of hexane solution was collected with a fraction collector and 80 ml of the fraction containing amyl-indoline-2-carboxylate was concentrated to give 1.15 g of (R)-amyl-indoline-2-carboxylate [(R)-Ia] having a specific rotatory power $[\alpha]_D^{25}-3.9°$ (c=1.0, ethanol) as a syrup.

To 1.15 g of the obtained [(R)-Ia] was added 10 ml of 1N sodium hydroxide and the hydrolysis reaction was carried out at room temperature for about 3 hours. After adjusting the pH of the reaction mixture to 5.0 with 1N hydrochloric acid, extraction was made with ethyl acetate four times (10 ml×4), followed by dehydration, concentration under reduced pressure and recrystallization in acetone-hexane (2.5 ml–0.5 ml) to give 0.58 g of (R)-indoline-2-carboxylic acid [(R)-II] having a specific rotatory power $[\alpha]_D^{25}-21.7°$ (c=1.0, DMFA).

EXAMPLES 100 AND 101

The immobilization, the asymmetric hydrolysis and the separation of the product were carried out as in Example 99 employing different strains of the microorganism to give the results as shown in Table 13. As the substrate, 4 g of [(R,S)-Ia] was loaded.

TABLE 13

| Ex. | Strain | Substrate specificity | Indoline-2-carboxylic acid [II*] | |
| --- | --- | --- | --- | --- |
| | | | (R)-form | (S)-form |
| | | | $[\alpha]_D^{25}$ (c = 1.0, DMFA), yield (g) | |
| 100 | Bacillus subtilis IFO 3013 | (R) | −24.3°, 0.82 | +28.1°, 0.34 |
| 101 | Aspergillus melleus IFO 4420 | (R) | −23.2°, 0.78 | +27.0°, 0.36 |

What we claim is:

1. A process for preparing an (R)-indoline-2-carboxylic acid having the formula [(R)-II]:

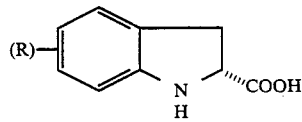

which comprises subjecting a racemic ester of an (R,S)-indoline-2-carboxylic acid having the formula [(R,S)-I)]:

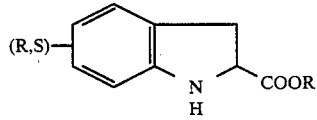

wherein R is an alkyl or alkenyl group having 1 to 10 carbon atoms; an alkyl or alkenyl group having 1 to 10 carbon atoms substituted with either hydroxyl group or a halogen atom, or simultaneously substituted with both hydroxyl group and a halogen atom; or a substituted or unsubstituted aromatic hydrocarbon group, to the action of an enzyme selected from the group consisting of Protease Amano P, Bioplase AL 15, Actinase E, Pancreatic digesting enzyme TA, Steapsin and Lipase L 3216, or a microorganism selected from the group consisting of Aspergillus melleus IFO 4420, Bacillus subtilis IFO 3018, Streptomyces griseus IFO 8358, Saccharomyces cerevisiae HUT 7018, Trichosporon cutaneum IFO 1200, Aeromonas hydrophila IFO 3820, Arthrobacter paraffineus ATCC 21317, Arthrobacter nicotianae IFO 14234, Acidiphilium cryptum IFO 14242, Brevibacterium protophormiae IFO 12128, Corynebacterium paurometabolum IFO 12160 and Pseudomonas oxalacticus IFO 13593, or a stereoselective esterase from any of these microorganisms, to asymmetrically hydrolyze the racemic ester [(R,S)-I] into optically active (R)-indoline-2-carboxylic acid [(R)-II] and an ester of (S-indoline-2-carboxylic acid having the formula [(S)-1]

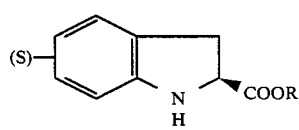

wherein R is as above, and then isolating the optically active (R)-indoline-2-carboxylic acid [(R)-II].

2. The process of claim 1, wherein said racemic ester of (R, S)-indoline-2-carboxylic acid [(R,S)-I] is subject to the action of said enzyme or microorganism immobilized on a hydrophobic support.

3. A process for preparing an (S)-indoline-2-carboxylic acid having the formula [(S)-II]:

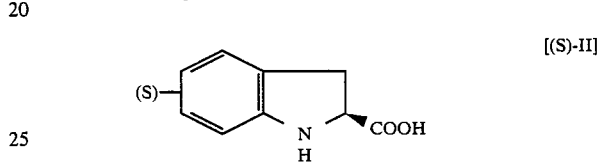

which comprises subjecting a racemic ester of an (R,S)-indoline-2-carboxylic acid having the formula [(R,S)-I]:

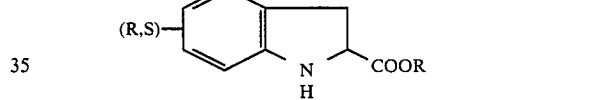

wherein R is an alkyl or alkenyl group having 1 to 10 carbon atoms; an alkyl or alkenyl group having 1 to 10 carbon atoms substituted with either hydroxyl group or a halogen atom, or simultaneously substituted with both hydroxyl group and a halogen atom, or a substituted or unsubstituted aromatic hydrocarbon group, to the action of an enzyme selected from the group consisting of Lipoprotein lipase and Lipase AP 6, or a microorganism selected from the group consisting of Pseudomonas aeruginosa IFO 3080, Aspergillus niger IFO 4407, Arthrinium phaeospermum IFO 5703, Aspergillus ficuum IFO 4280, Cephalosporium mycophilum IFO 8580, Echinopodospora jamaicensis IFO 30406, Emericellopsis glabra IFO 9031, Hypocrea lactea IFO 8434, Isaria atypicola IFO 9205, Lepista nuda IFO 8104, Nectria flammea IFO 30306, Pestalotiopsis distincta IFO 9981, Phialophora fastigiasta IFO 6850, Podospora carbonaria IFO 30924, Botryoascus synnaedendrus IFO 1604, Candida diversa IFO 1090, Citeromyces matritensis IFO 0651, Debaryomyces hansenii IFO 0015, Hormoascus platypodis IFO 1471, Moniliella tomentosa CBS 22032, Kluyveromyces fragilis IFO 0288, Nadsonia elongata IFO 0665, Rhodotorula glutinis IAM 4642, Schizosaccharomyces pombe IFO 0347, Torulopsis gropengiesseri IFO 0659, Wickerhamia fluorescens IFO 1116, Alcaligenes faecalis IFO 12669, Arthrobacter crystallopoietes IFO 14235, Brevibacterium flavum ATCC 21269, Protaminobacter alboflavus IFO 3707 and Pseudomonas acidovorans IFO 13582, or a stereoselective esterase from any of these microorganisms, to asymmetric hydrolyze the racemic ester [(R,S)-I] into optically active (S)-indoline-2-carboxylic acid [(S)-II] and an ester of (R)-indoline-2-carboxylic acid having the formula [(R)-I]:

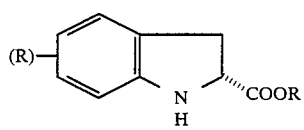
[(R)-I]

wherein R is as above, and then isolating the optically active (S)-indoline-2-carboxylic acid [(S)-II].

4. The process of claim 3, wherein said racemic ester of (R,S)-indoline-2-carboxylic acid [(R,S)-I] is subjected to the action of said enzyme or microorganism immobilized on a hydrophobic support.

5. A process for preparing an (R)-indoline-2-carboxylic acid having the formula [(R)-II]:

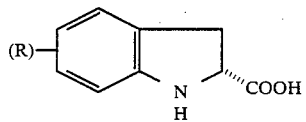
[(R)-II]

and an (S)-indoline-2-carboxylic acid having the formula [(S)-II]:

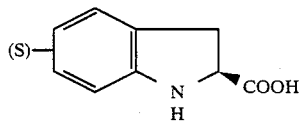
[(S)-II]

which comprises:
(a) contacting a racemic ester of (R,S)-indoline-2-carboxylic acid having the formula [(R,S)-I]:

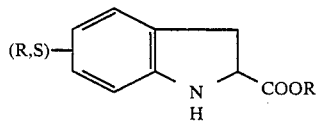
[(R,S)-I]

wherein R is an alkyl or alkenyl group having 1 to 10 carbon atoms; an alkyl or alkenyl group having 1 to 10 carbon atoms substituted with either hydroxyl group or halogen atom, or simultaneously substituted with both hydroxyl group and a halogen atom; or a substituted or unsubstituted aromatic hydrocarbon group, with an enzyme selected from the group consisting of Protease Amano P, Bioplase AL 15, Actinase E, Pancreatic digesting enzyme TA, Steapsin and Lipase L 3216, or a microorganism selected from the group consisting of *Aspergillus melleus* IFO 4420, *Bacillus subtilis* IFO 3018, *Streptomyces griseus* IFO 8358, *Saccharomyces cerevisiae* HUT 7018, *Trichosporon cutaneum* IFO 1200, *Aeromonas hydrophila* IFO 3820, *Arthrobacter paraffineus* ATCC 21317, *Arthrobacter nicotianae* IFO 14234, *Acidiphilium cryptum* IFO 14242, *Brevibacterium protophormaiae* IFO 12128, *Corynebacterium paurometabolum* IFO 12160 and *Pseudomonas oxalacticus* IFO 12160, or a stereoselective esterase from any of thee microorganisms, immobilized on a hydrophobic support to asymmetrically hydrolyze said racemic ester [(R,S)-I] into optically active hydrophilic (R)-indoline-2-carboxylic acid [(R)-II] and an ester of (S)-indoline-2-carboxylic acid having the general formula [(S)-I]

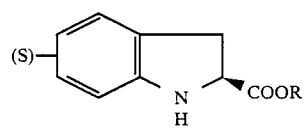
[(S)-I]

wherein R is as above,
(b) eluting the (R)-indoline-2-carboxylic acid [(R)-II], and
(c) hydrolyzing the ester of (S)-indoline-2-carboxylic acid [(S)-I] with an alkali to form (S)-indoline-2-carboxylic acid [(S)-II] and eluting the thus formed (S)-indoline-2-carboxylic acid [(S)-II].

6. A process for preparing an (R)-indoline-2-carboxylic acid having the formula [(R)-II]:

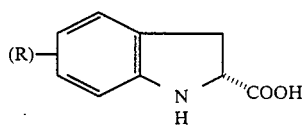
[(R)-II]

and an (S)-indoline-2-carboxylic acid having the formula [(S)-II]:

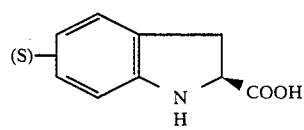
[(S)-II]

which comprises
(a) contacting a racemic ester of (R,S)-indoline-2-carboxylic acid having the formula [(R,S)-I]:

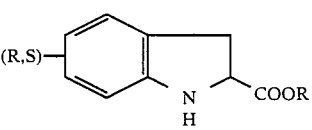
[(R,S)-I]

wherein R is an alkyl or alkenyl group having 1 to 10 carbon atoms; an alkyl or alkenyl group having 1 to 1 carbon atoms substituted with either hydroxyl group or a halogen atom, or simultaneously substituted or unsubstituted aromatic hydrocarbon group, with an enzyme selected from the group consisting of Lipoprotein lipase and Lipase AP 6, or a microorganism selected from the group consisting of *Pseudomonas aeruginosa* IFO 3080, *Aspergillus niger* IFO 4407, *Arthrinium phaeospermum* IFO 5703, *Aspergillus ficuum* IFO 4280, *Cephalosporium mycophilum* IFO 8580, *Echinopodospora jamaicensis* IFO 30406, *Emericellopsis glabra* IFO 9031, *Hypocrea lactea* IPO 8434, *Isaria atypicola* IFO 9205, *Lepista nuda* IFO 8104, *Nectria flammea* IFO 30306, *Pestalotiopsis distincta* IFO 9981, *Phialophora fastigiasta* IFO 6850, *Podospora carbonaria* IFO 30294, *Botryoascus synnaedendrus* IFO 1604, *Candida diversa* IFO 1090, *Citeromyces matritensis* IFO 0651, *Debaryomyces hansenii* IFO 0015, *Hormoascus platypodis* IFO 1471, *Moniliella tomentosa*

CBS 22032, *Kluyveromyces fragilis* IFO 0288, *Nadsonia elongata* IFO 0665, *Rhodotorula glutinis* IAM 4642, *Schizosaccharomyces pombe* IFO 0347, *Torulopsis gropengiesseri* IFO 0659, *Wikerhamia fluorenscens* IFO 1116, *Alcaligenes faecalis* IFO 12669, *Arthrobacter crystallopoietes* IFO 14235, *Brevibacterium flavum* 21269, *Protaminobacter alboflavus* IFO 3707 and *Pseudomonas acidovorans* IFO 13582, or a stereoselective esterase from any of these microorganisms, immobilized on a hydrophobic support to asymmetrically hydrolyze said racemic ester [(R,S)-I] into optically active hydrophilic (S)-indoline-2-carboxylic acid [(S)-II] and an ester of (R)-indoline-2-carboxylic acid having the general formula [(R)-I]:

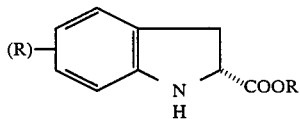

wherein R is as above,
(b) eluting hydrophilic (S)-indoline-2-carboxylic acid [(S)-II],
(c) hydrolyzing said ester of (R)-indoline-2-carboxylic acid [(R)-I] with an alkali to form (R)-indoline-2-carboxylic acid [(R)-II] and eluting the thus formed (R)-indoline-2-carboxylic acid [(R)-II].

7. The process of claims 2, 4, 5 or 6, wherein said hydrophobic support for immobilizing the enzyme or microorganism is a member selected from the group consisting of a synthetic adsorbent, a hydrophobic resin for chromatography, a hydrophobic photo induced crosslinked-resin and a macromolecule material in which a hydrophobic group is introduced by a chemical bonding.

8. The process of claim 2, 4, 5 or 6, wherein said asymmetric hydrolysis is carried out with said immobilized enzyme or microorganism filled in a column.

9. The process of claim 2, 4, 5 or 6, wherein said asymmetric hydrolysis is carried out in a batch process.

* * * * *

UNITED STATES PATENT AND TRADEMARK OFFICE
CERTIFICATE OF CORRECTION

PATENT NO. : 4,898,822

DATED : February 6, 1990

INVENTOR(S) : ASADA et al

It is certified that error appears in the above-identified patent and that said Letters Patent is hereby corrected as shown below:

On the cover page, Item [75], "Hidetoshi Katsuki" should read

--Hidetoshi Kutsuki--.

Signed and Sealed this

Twenty-first Day of May, 1991

Attest:

HARRY F. MANBECK, JR.

Attesting Officer

Commissioner of Patents and Trademarks